US007313481B2

(12) United States Patent
Moos et al.

(10) Patent No.: US 7,313,481 B2
(45) Date of Patent: Dec. 25, 2007

(54) METHODS AND DEVICES FOR ANALYZING AND CONTROLLING THE PROPAGATION OF WAVES IN A BOREHOLE GENERATED BY WATER HAMMER

(75) Inventors: Daniel Moos, Palo Alto, CA (US); Youli Quan, Fremont, CA (US)

(73) Assignee: GeoMechanics International, Inc., Houston, TX (US)

( * ) Notice: Subject to any disclaimer, the term of this patent is extended or adjusted under 35 U.S.C. 154(b) by 0 days.

(21) Appl. No.: 11/440,885

(22) Filed: May 25, 2006

(65) Prior Publication Data
US 2006/0293857 A1 Dec. 28, 2006

Related U.S. Application Data

(60) Provisional application No. 60/684,632, filed on May 25, 2005.

(51) Int. Cl.
*G01N 15/08* (2006.01)
*E21B 21/08* (2006.01)
(52) U.S. Cl. ...................................... 702/12; 73/152.22
(58) Field of Classification Search .................. 702/12, 702/11; 73/152.01, 152.05, 152.18, 152.21, 73/152.22, 152.29, 152.37–38, 152.51, 152.27; 175/1; 703/9, 10
See application file for complete search history.

(56) References Cited

U.S. PATENT DOCUMENTS

| 4,252,209 | A | * | 2/1981 | Silverman | 181/106 |
|---|---|---|---|---|---|
| 4,783,769 | A | * | 11/1988 | Holzhausen | 367/35 |
| 4,802,144 | A | * | 1/1989 | Holzhausen et al. | 367/35 |
| 5,170,378 | A | * | 12/1992 | Mellor et al. | 367/86 |
| 5,220,504 | A | * | 6/1993 | Holzhausen et al. | 702/12 |
| 5,741,978 | A | * | 4/1998 | Gudmundsson | 73/861.04 |
| 6,237,701 | B1 | * | 5/2001 | Kolle et al. | 175/1 |

FOREIGN PATENT DOCUMENTS

WO    WO0225062 A1    3/2002

OTHER PUBLICATIONS

Patzek et al., Lossy Transmission Line Model of Hydrofractured Well Dynamics, 2000, Journal of Petroleum Science and Engineering 25, pp. 59-77.*
Chen et al.; *Seismogram synthesis for radially layered media using the generalized reflection/transmission coefficients method: Theory and applications to acoustic logging*, Geophysics, vol. 61, No. 4 (Jul.-Aug. 1996); pp. 1150-1159, 8 Figs., 7 Tables.

(Continued)

*Primary Examiner*—John Barlow
*Assistant Examiner*—Toan M. Le
(74) *Attorney, Agent, or Firm*—Madan, Mossman & Sriram, P.C.

(57) ABSTRACT

A method for simulating water-hammer waves in a borehole is used to estimate formation parameters such as porosity and permeability, and to design completion strings. The simulation method uses a model that has a plurality of layers, at least one of the layers includes radial layering. Determined formation properties from analysis of the water-hammer are used in development operations.

16 Claims, 17 Drawing Sheets

OTHER PUBLICATIONS

F.J. Santarelli et al.; *Sand Production on Water Injectors: How Bad Can It Get?*, SPE Drill. & Completion vol. 15, No. 2, Jun. 2000, pp. 132-139.

Bakulin et al.; *Tube-wave relection from a porous permeable layer with an idealized perforatio*/EG/Houston 2005 Annual Meeting, pp. 332-335.

Tezuka et al.; *Modeling of low-frequency Stoneley-wave propagation in an irregular borehole*, Geophysics, vol. 62, No. 4, (Jul.-Aug. 1997), pp. 1047-1058, 12 Figs., 2 Tables.

Jardine et al.; *Hard or Soft Shut-In: Which is the Best Approach?*, SPE/IADC 25712, 1993 SPE/IADC Drilling Conference, Feb. 23-25, 1993, pp. 359-370.

Hardin: *Fracture Characterization from Attenuation and Generation of Tube Waves*, Department of Earth, Atmospheric, and Planetary Sciences, Feb. 7, 1986, pp. 1-2.

Tichelaar et al.; *Modeling of borehole Stoneley waves in the presence of skin effects*, J. Acoust. Soc. Am., vol. 105, No. 2, Pt. 1, Feb. 1999, pp. 601-609.

Zhao; *Effects of hetergeneities on Fluid Flow and Borehole Permeability Measurements*; Department of Earth, Atmospheric, and Planetary Sciences, May 1, 1994, pp. 1-2.

Patzek et al., *Lossy Transmission Line Model of Hydrofractured Well Dynamics*, pp. 1-11, 1998.

Paige et al.; *Field Application of Hydraulic Impedance Testing for Fracture Measurements*, SPE Production & Facilities, Feb. 1995, pp. 7-12.

Rachford, Jr. et al.; *Application of Variational Methods to Tranient Flow in Complex Liquid Transmission Systems*, SPE, Jul. 1, 1975, pp. 151-166, 10 Figs.

Tseng, *Momentum Pronciple (Chapter 6a)*, Department of Civil and Environmental Engineering, CEE 100 Elementary Fluid Mechanics, Lecture 6a, May 12, 2006, (no longer on the web) pp. 1-14.

Bergant et al., *Furthur Investigation of Parameters Affecting Water Hammer Wave Attenuation, Shape and Timing Part 1: Mathematical Tools*, 11th International Meeting of the IAHR Work Group on the Behaviour of Hydraulic Machinery under Steady Oscillatory Conditions, Stuttgart, Germany, (2003), pp. 1-12.

Bergant et al., *Furthur Investigation of Parameters Affecting Water Hammer Wave Attenuation, Shape and Timing Part 2: Mathematical Tools*, http://www.ihs.uni-stuttgart.de/iahr2003/TableOfContents/Session4/Bergant%20Part%202.pdf , (2003) pp. 1-11.

* cited by examiner

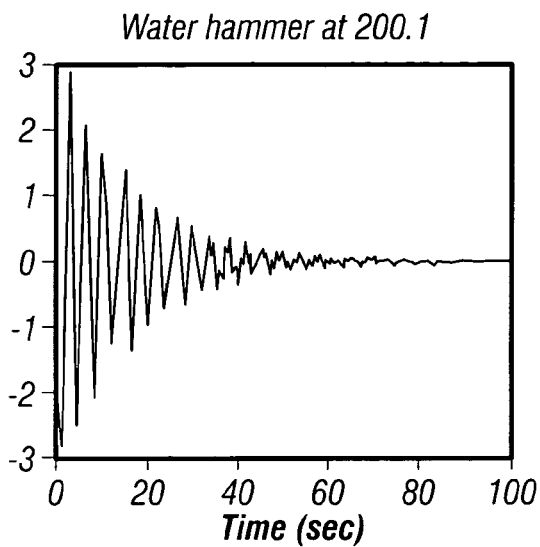
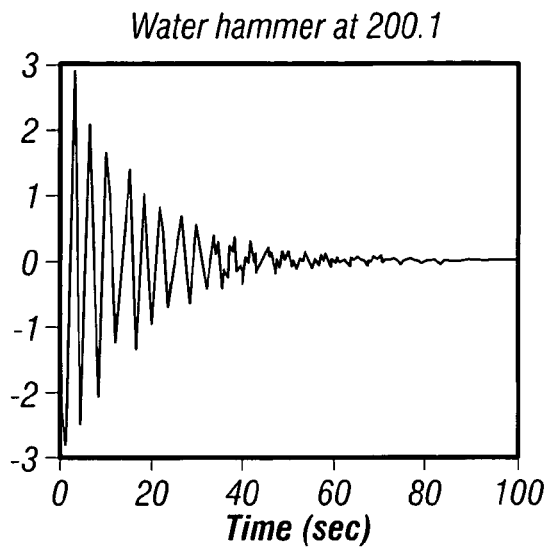
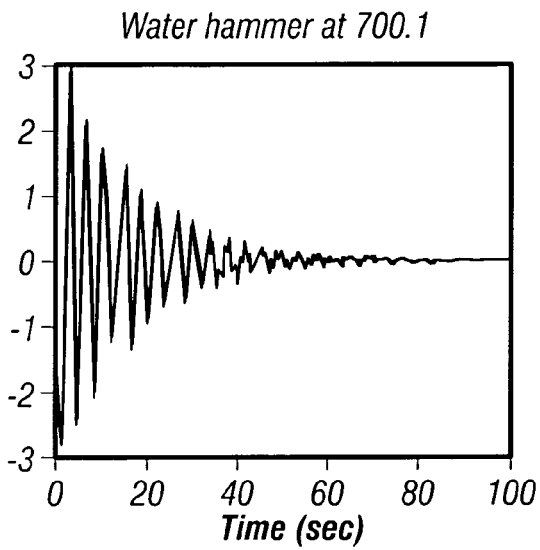
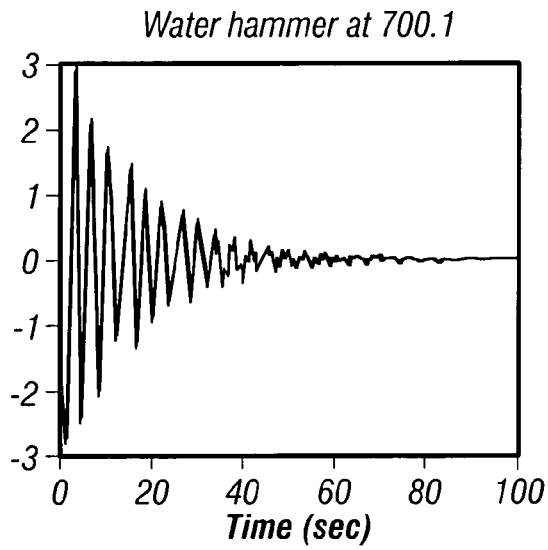
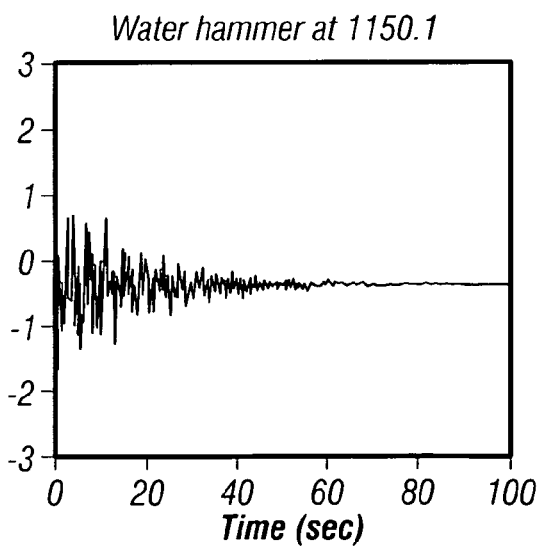
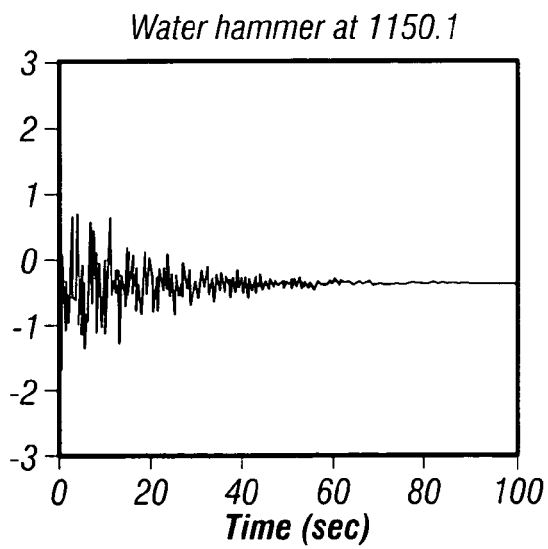
FIG. 15a                    FIG. 15b

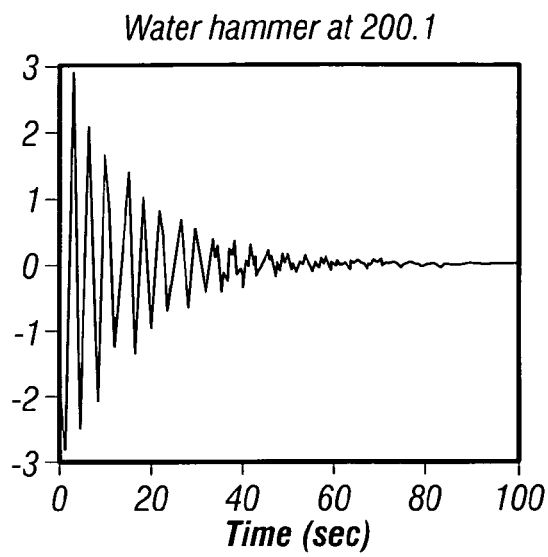
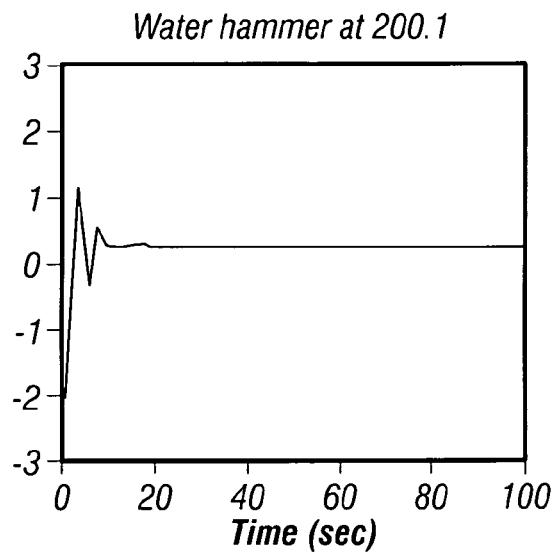
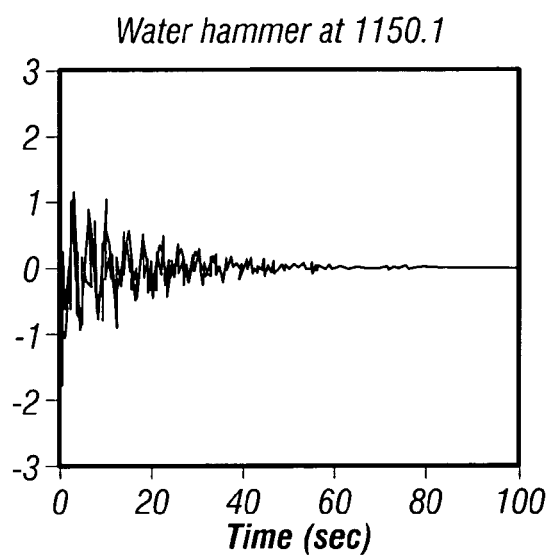
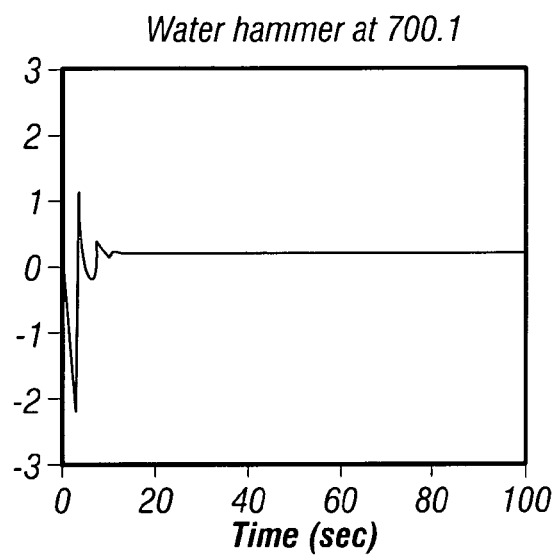
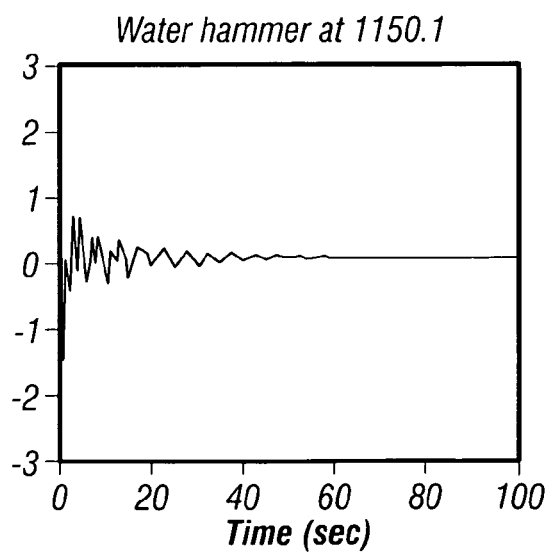
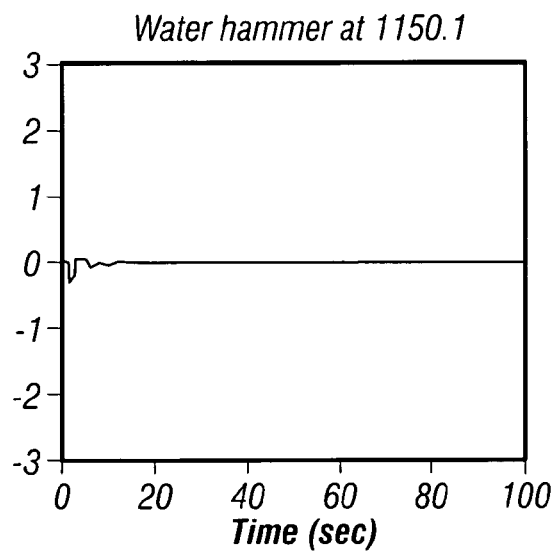
FIG. 15c                    FIG. 15d

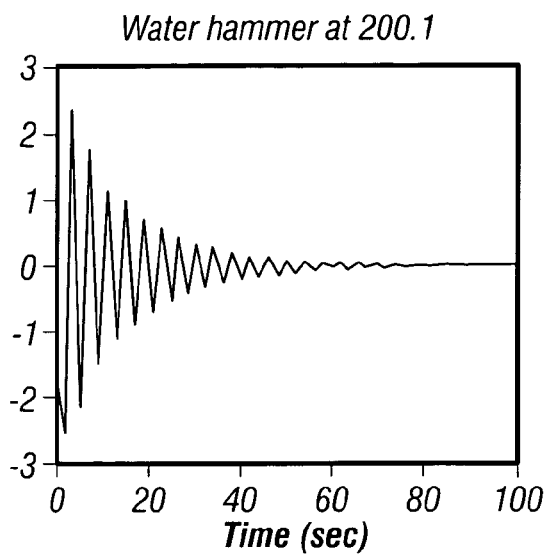
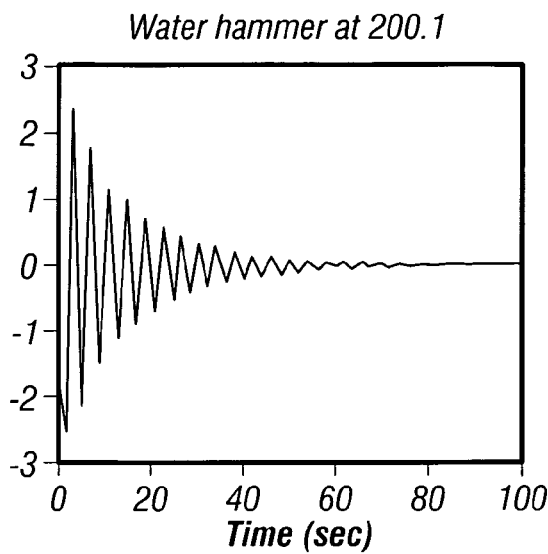
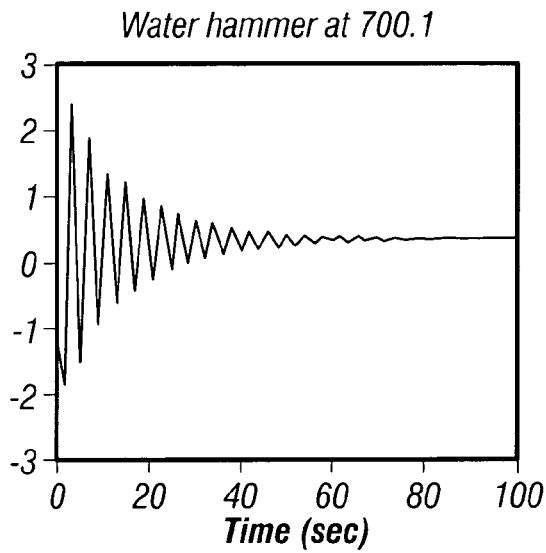
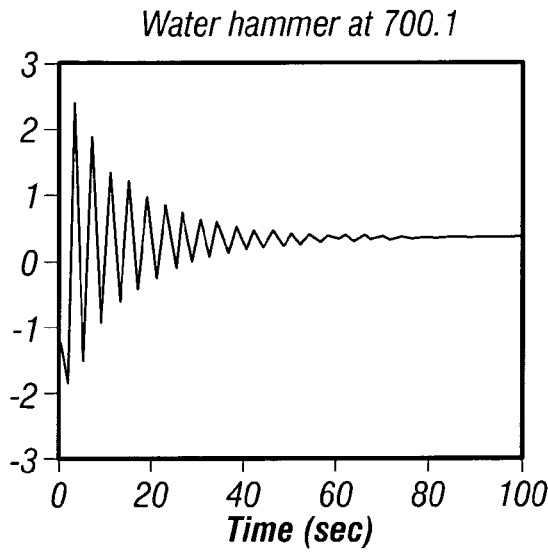
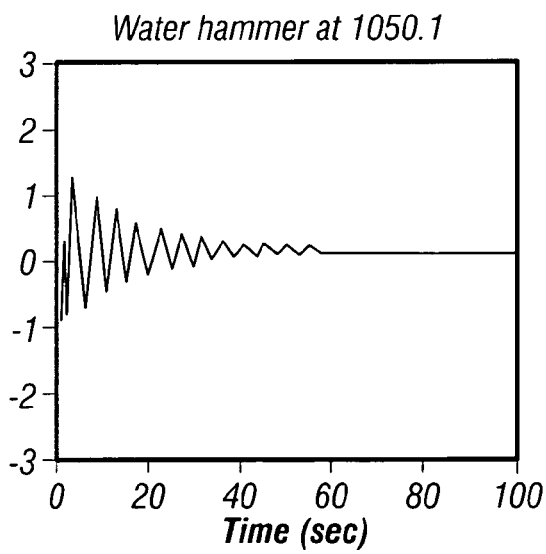
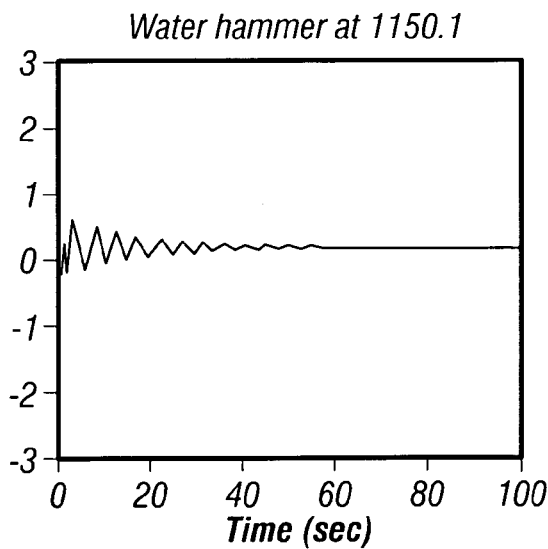
FIG. 15e    FIG. 15f

METHODS AND DEVICES FOR ANALYZING AND CONTROLLING THE PROPAGATION OF WAVES IN A BOREHOLE GENERATED BY WATER HAMMER

CROSS-REFERENCES TO RELATED APPLICATIONS

This application claims priority from U.S. Provisional Patent Application Ser. No. 60/684,632 filed on May 25, 2005.

BACKGROUND OF THE INVENTION

1. Field of Invention

The present invention relates to methods for analyzing the effects of borehole, formation, fluid, and completion properties on the propagation of waves generated by water hammer. In another aspect, the present invention relates to methods and devices for mitigating the effect of water hammer in borehole completion equipment and in injectors. The invention can also be used to determine the properties and the changes in properties of completion and formation.

2. Description of the Related Art

Water hammer (or, more generally, fluid hammer) is a pressure surge or wave generated by the kinetic energy of a fluid in motion when it is forced to stop or change direction suddenly. For example, if a valve is closed suddenly at an end of a pipeline system a water hammer wave propagates in the pipe. In a production well or in a well being drilled, a water hammer may be produced if a blowout preventer (BOP) is activated in response to a detected influx of gas or fluid into a borehole. A water hammer may also be generated during a standard shut-in of a well. See, for example, SPE 00064297. The transient pressure associated with a water hammer may cause borehole failure and/or failure of sensitive electronic, electrical and electromechanical equipment in a well. For the purposes of the present invention, we refer to a "borehole system" as including the borehole and all devices attached to the borehole.

U.S. Pat. No. 5,220,504 to Holzhausen et al. discloses a method of determining formation properties such as permeability by setting up pressure oscillations in a borehole. The analysis is based on modeling of the earth as a homogenous medium (with possible fractures therein) surrounding a fluid filled borehole. The methodology is of little use in a real production borehole which may include production tubing, casings of different sizes, cement, perforations, packers and sand-packing. The present invention is directed towards analysis of real production boreholes that may have both radial and vertical variations.

SUMMARY OF THE INVENTION

One embodiment of the invention is a method of determining a property of an earth formation. A fluid hammer is generated in a borehole in the earth formation, the fluid hammer producing a pressure pulse in the fluid. A measurement indicative of the fluid pressure is made at least one location in the borehole. A value of the property of the formation is estimated using the measurement. Generating the fluid hammer may be done by opening a flow control device in the borehole system and/or closing a flow control device in the borehole system. The pressure pulse propagates in the borehole with a velocity determined at least in part by a shear velocity of the formation. Estimating the property pf the formation may be done by defining a model of the borehole and the earth formation, the model including a plurality of layers with at least one of the plurality of layers including radial layering. Estimating the property of the formation may further include simulating an output of the model and comparing the simulated output with the measurement. Simulating the output of the model includes using transmission and reflection coefficients at layer boundaries. The estimate property may include formation porosity, formation permeability and formation damage. The method may also include repeating the generation of the water hammer at a later time and determining a change in the value of the property.

Another embodiment of the invention is a method of developing a reservoir in an earth formation. The method includes defining a model of the earth formation and a borehole therein. The model includes a plurality of layers, at least one of the layers includes radial layering. The response of the model to a fluid hammer is simulated and the output is used to determine a parameter of a completion string in the borehole and/or an operating parameter of a flow control device in the borehole. Using the output of the model may include identifying a maximum pressure of a fluid in the borehole and wherein the operating parameter of the flow control device may include a rate of operation of the flow control device. The flow control device may be at a surface location, a downhole location, and/or a downhole location in a side borehole. Determining the parameter of the completion string may include selecting a borehole diameter, selecting a borehole shape, selecting a material of a casing, selecting a material of a tubing; selecting a property of a cement, selecting a property of a fluid in the borehole, and/or selecting a property of a coupling between two sections of casing. Determining the parameter of a casing completion string may include determining a parameter of a wave reflector section, a wave attenuator section, a size of a perforation, a shape of a perforation, and/or positioning of a perforation. Determining a parameter of a completion string may include determining a parameter of a screen and/or a gravel pack. Determining a parameter of a completion string may include determining a dimension of a diameter change, an interval distance between diameter changes, and the number of diameter changes.

Another embodiment of the invention is a computer readable medium for use with a method of determining a property of an earth formation. The method includes generating a fluid hammer in a borehole in the earth formation, the fluid hammer generating a pressure pulse in the fluid. The method further includes making a measurement indicative of a fluid pressure at least one location in the borehole. The medium includes instructions that enable a processor to estimate a value of the property of the formation using measurement. The medium may include a ROM, an EPROM, an EAROM, a flash memory, and/or an optical disk.

BRIEF DESCRIPTION OF THE DRAWINGS

For detailed understanding of the present invention, references should be made to the following detailed description of the preferred embodiment, taken in conjunction with the accompanying drawings, in which like elements have been given like numerals and wherein:

FIG. 2b illustrates simulated water hammer waves at the top, middle and bottom of the borehole of FIG. 2a;

FIG. 5b shows the simulated pressure field at the top, middle and bottom of the borehole of FIG. 5a;

FIGS. 9b and 9c are graphs illustrating wave forms at selected locations along the completion system of FIG. 9a;

FIGS. 10b and 10c are graphs illustrating wave forms at selected locations along the completion system of FIG. 10a;

FIGS. 11b and 11c are graphs illustrating wave forms at selected locations along the completion system of FIG. 11a;

FIGS. 12b, 12c and 12d are graphs illustrating wave forms at selected locations along the completion system of FIG. 12a;

FIGS. 13b and 13c are graphs illustrating wave forms at selected locations along the completion system of FIG. 13a;

FIG. 15a shows simulated pressure measurements for a cased hole with 200 m of smaller casing below it;

FIG. 15b shows simulated pressure measurements for a cased hole with 200 m of open hole with 0.5 mD permeability below;

FIG. 15c shows simulated pressure measurements for a cased hole with 200 m of open hole with 5 mD permeability below;

FIG. 15d shows simulated pressure measurements for a cased hole with 200 m of open hole with 500 mD permeability below;

FIG. 15e shows simulated pressure measurements for a cased hole with 200 m of damaged open hole with 30 D permeability and 10 cm of damaged hole with 20 mD permeability below; and FIG. 15f shows simulated pressure measurements for a cased hole with 200 m of damaged open hole with 300 mD permeability and 1 cm of damaged hole with 20 mD permeability below.

DETAILED DESCRIPTION OF THE INVENTION

Figure 1:
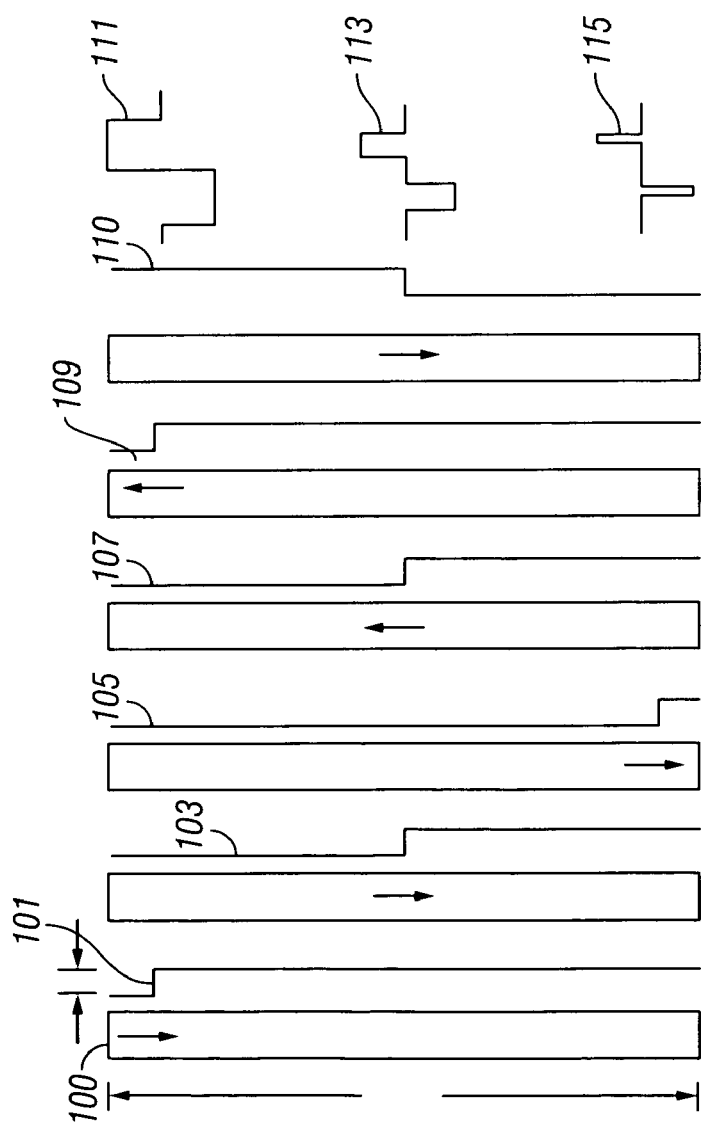
FIG. 1 illustrates a simple water hammer and water hammer waves at the top, middle and bottom.

The present invention is based on analysis of water hammer signals propagating in a borehole. Suppose that water is being injected into a borehole with a flow velocity $V_0$. If a valve is suddenly closed at the wellhead, then a pressure wave is generated and propagates downwards. FIG. 1 demonstrates a simple water hammer wave in a borehole. The amplitude of the pressure wave can be determined by the approximate relation $$\Delta P = c\rho_0 V_0 \tag{1}$$

where $\rho_0$ is fluid density in the borehole, and c is the wave propagation speed. We will discuss how to determine speed c under different borehole conditions. When the wave reaches the bottom of the borehole, it reflects, propagates upwards, and then bounces back from top of the borehole again. This phenomenon is called water hammer and studied in water supply area. Ideally, this up-down procedure repeats forever with a vibration frequency $$f = \frac{c}{4L} \tag{2}$$

Here, L is the depth range of the borehole. In the real world, however, the wave will decay slowly due to attenuation caused by surrounding porous rocks and other factors. The vibration frequency and the decay curve along with other observable features from water hammer waves can be used to investigate the porous properties of surrounding porous rocks. The velocity in eqn. (2) will correspond to the velocity of the water hammer and is different from the compressional wave velocity in eqn. (1). The frequency here is related to the repetition rate of the water hammer and is different from the frequency of the shock wave that comprises the water hammer.

Figure 3:
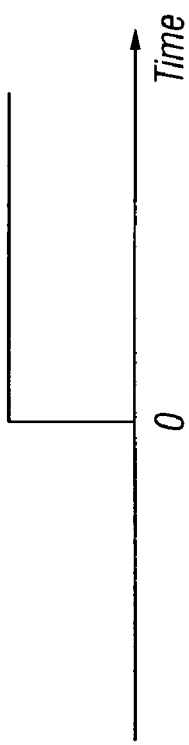
FIG. 3 shows a step time function as the source of water hammer simulation.

Referring to FIG. 1, a series of snapshots of an exemplary water hammer pulse 101, 103, 105, 107, 109 in a borehole 100 are shown. The pulse is shown starting at the top of the borehole 101, as near the middle of the borehole as 103, just before reaching the bottom of the borehole as 105, after reflection from the bottom of the borehole and near the middle of the borehole as 107, just before reaching the top of the borehole as 109. Following this, the pulse undergoes another reflection at the top of the borehole and is shown halfway down the borehole as 110. The arrows in the figure indicate the direction in which the water hammer pulse is propagating. Also shown in FIG. 1 are exemplary time series representations 111, 113 and 115 that would be measured at locations near the top, near the middle and near the bottom of the borehole respectively. The pulse for the example is a step function such as that shown in FIG. 3. The reflection coefficients at the top and bottom of the borehole are a function of the impedance contrasts at those locations.

Figure 2A:
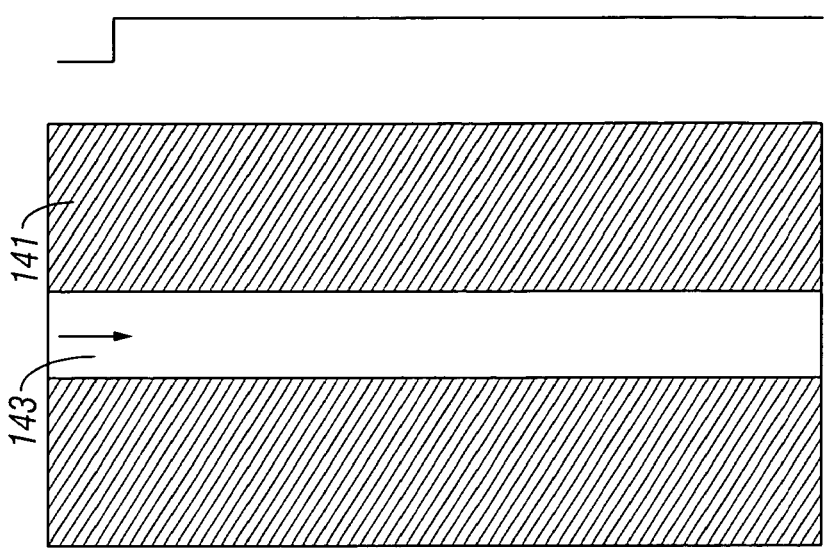
FIG. 2a illustrates a simple borehole in a homogenous formation.

FIG. 2a shows an exemplary borehole 143 in a homogenous earth formation 141. For the simple fluid-filled borehole shown in FIG. 2a, according to eqn (2), we know the frequency of water hammer wave is very low. For example, if L=500 m, c=1500 m/s (upper limit of water-filled borehole), then, according to equation 2, f=0.75 Hz. In the present invention, we use low frequency tube waves to simulate the water hammer. For a low frequency tube wave, it can be approximated as a 1-D problem. White (1983) derived formulas calculating velocities of low frequency tube waves in different cases. For a borehole in a non-permeable elastic formation, the velocity of tube waves is $$c = \frac{1}{\left[\rho\left(\frac{1}{B} + \frac{1}{\mu}\right)\right]^{1/2}}, \quad (3)$$

where $B=\rho_f V_f^2$ is the fluid bulk modulus, $\mu=\rho V_s^2$ is a formation shear modulus, $\rho$ is the formation density, $V_s$ is a formation shear velocity, $\rho_f$ is the fluid density and $V_f$ is the fluid velocity (the velocity of compressional waves in the fluid). For a borehole in a permeable porous formation, the complex tube wave velocity is:

$$c = \left[\rho\left(\frac{1}{B} + \frac{1}{\mu} + \frac{2}{i\omega b}\frac{1}{Z}\right)\right]^{-1/2} \quad (4a)$$

$$\frac{1}{Z} = \frac{\kappa}{\eta a}\frac{\sqrt{i\omega m}\, aK_1(\sqrt{i\omega m}\, a)}{K_0(\sqrt{i\omega m}\, a)}. \quad (4b)$$

Here, $m=\phi\eta/(\kappa B)$, $\kappa$ is the formation permeability, $\phi$ porosity, a borehole radius, $\eta$ viscosity. $K_0$ and $K_1$ are modified Bessel function of orders 0 and 1, respectively.

Figure 2B:
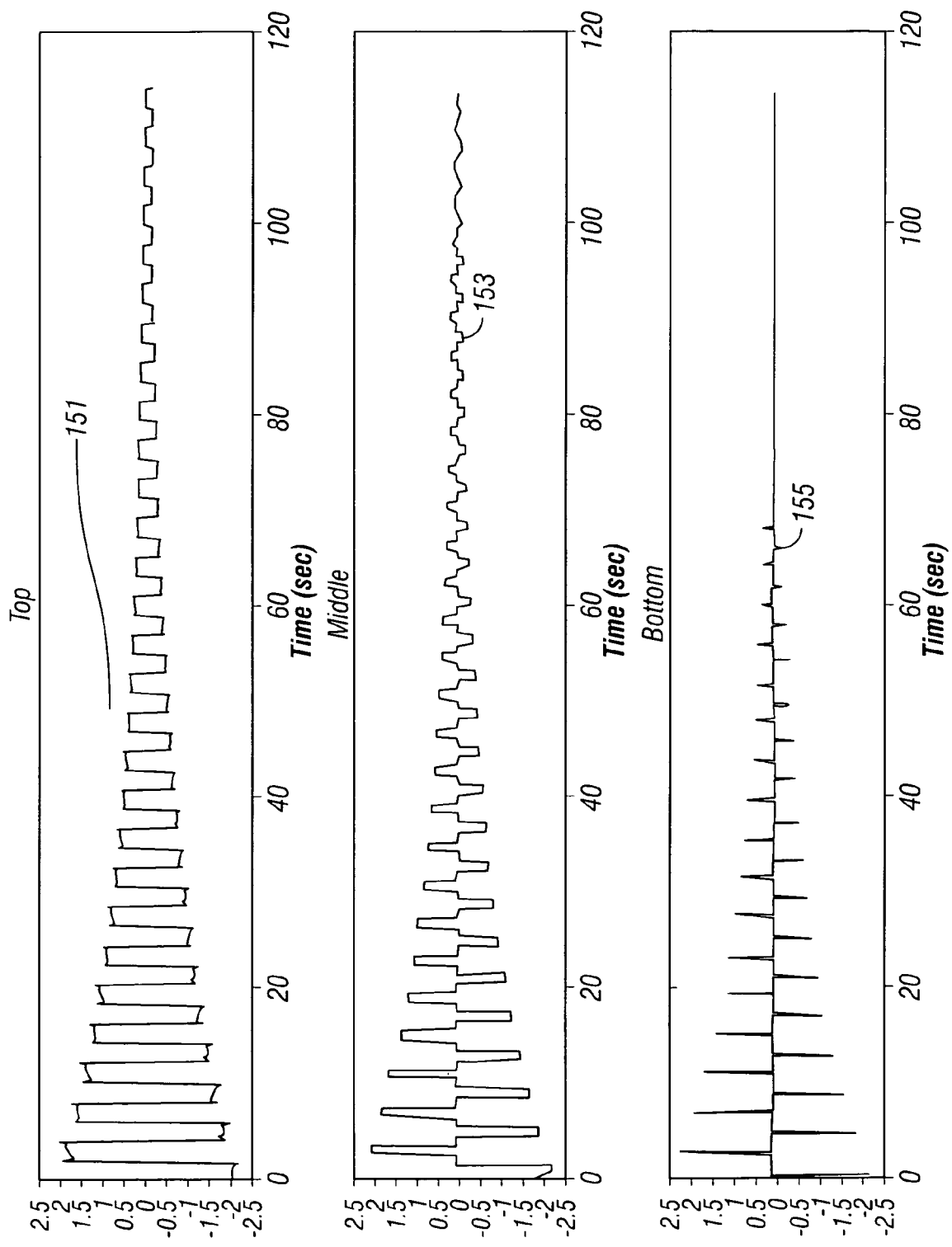

It should be noted that in a transversely isotropic medium, the velocity $V_f$ that determines the speed of the water hammer is the shear wave velocity for a horizontally polarized shear wave traveling horizontally (perpendicular to the symmetry axis). Shown in FIG. 2b are simulated water hammer waves recorded at the top 151, middle 153 and bottom 155 of the borehole. We next discuss how to model water hammer waves in complicated or irregular boreholes. For this we rely on the extensive prior art on the modeling of tube waves in simpler geometries.

Figure 4B:
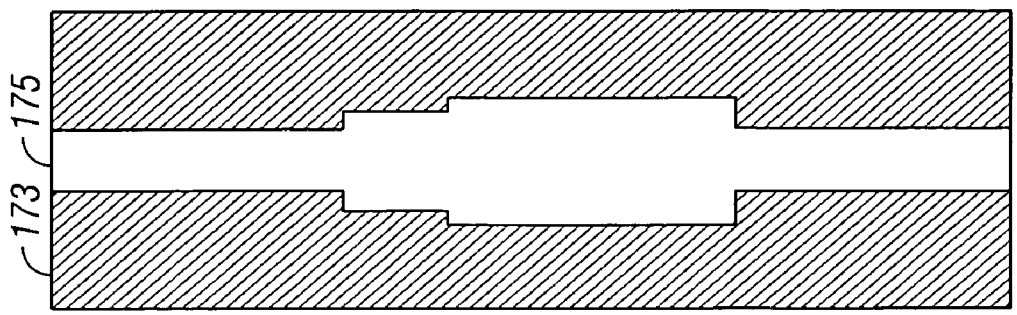
FIG. 4b shows a borehole with irregular diameters in a homogenous formation.
Figure 4A:
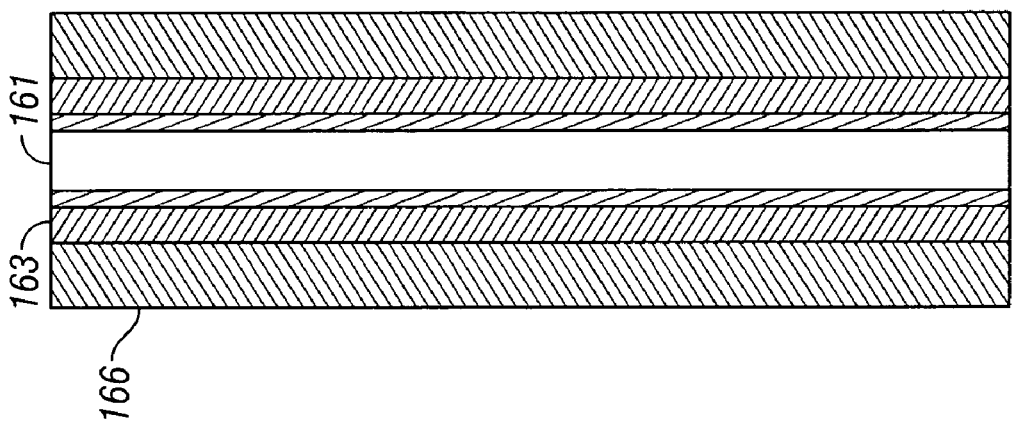
FIG. 4a shows radial layering in a borehole.
Figure 4C:
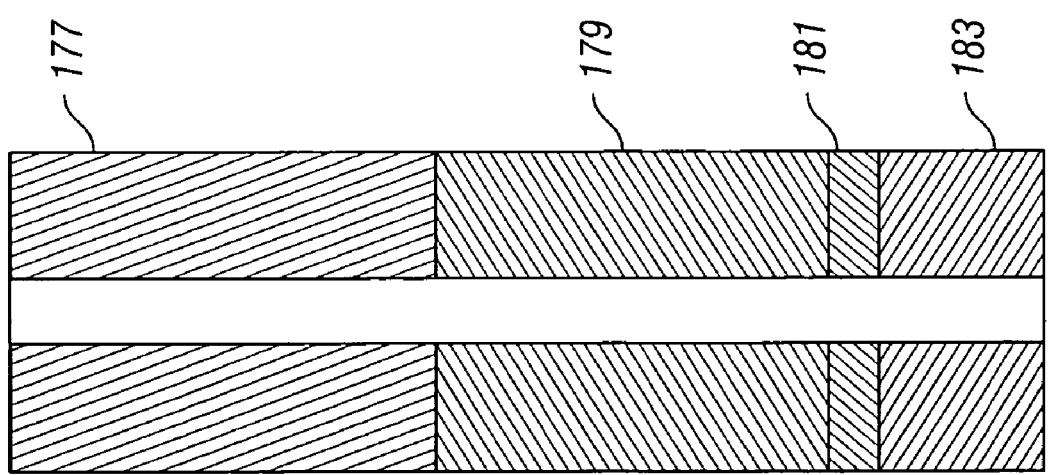
FIG. 4c shows a borehole in a horizontally layered earth formation.

Some of the existing results of tube wave modeling are adapted for our modeling of water hammer in complicated boreholes. Shown in FIG. 4a is a borehole 161 with radial concentric layers denoted by 163 and 165. FIG. 4b shows a borehole 175 having an irregular radius in a homogenous earth formation 173. FIG. 4c shows a borehole in a layered earth formation with layers 177, 179, 181, 183. The irregularities included borehole diameter changes and formation property changes.

Similar to the simple borehole case, for the purpose of illustration we here also treat water hammer waves in complicated boreholes as 1-D low frequency tube waves with a step source function. In this 1-D wave propagation problem, the borehole is divided into horizontal layers at depths where media property changes and/or borehole geometry changes occur. The reflection and transmission coefficients in a two-layer case are given by:

$$R = \frac{a_1 k_1 - a_2 k_2}{a_1 k_1 + a_2 k_2}, \quad (5)$$

$$T = \frac{2 a_1 k_1}{a_1 k_1 + a_2 k_2}. \quad (6)$$

Figure 5A:
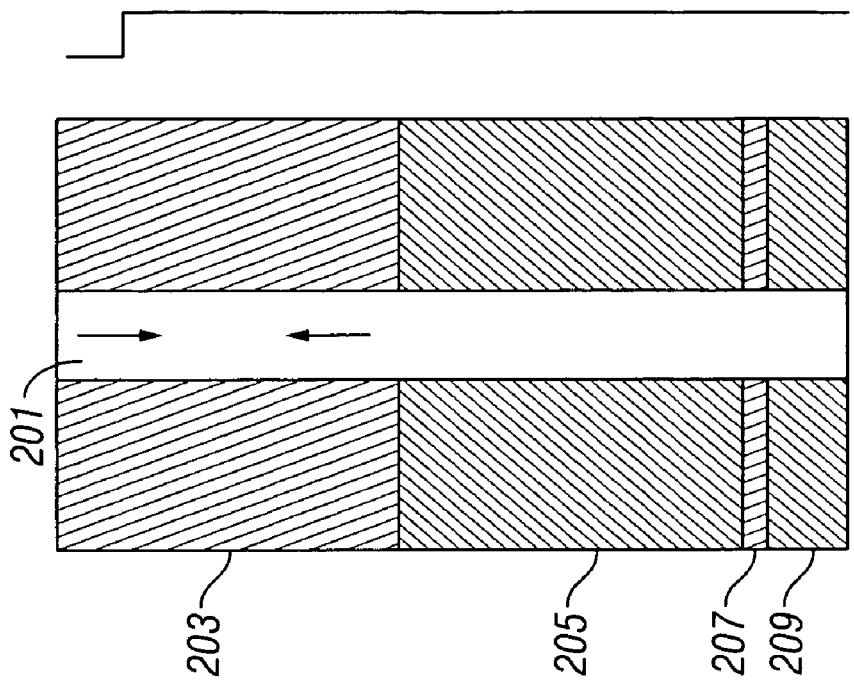
FIG. 5a shows a water hammer wave in a borehole with a layered earth formation.
Figure 5B:
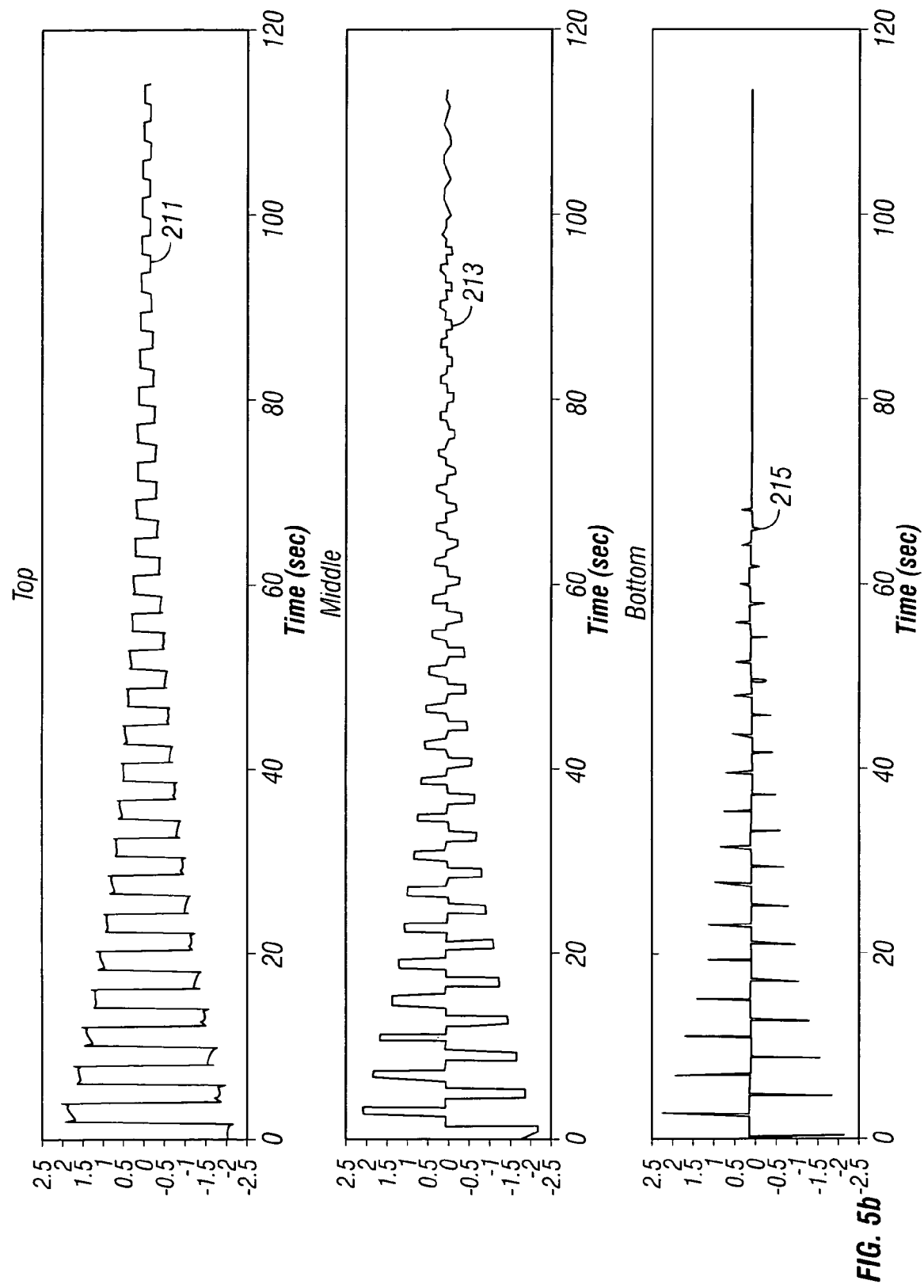

Here, waver numbers $k_1=\omega/c_1$ and $k_2=\omega/c_2$, radii $a_1$ and $a_2$ correspond to upper and lower layers. If there is no radial layering in a horizontal layer, eqn (3), (4) or other numerical methods can be used to calculate tube wave velocities $c_1$ and $c_2$. FIGS. 5a and 5b show an example of wave hammer in a complicated borehole.

The tube wave velocity in 203 is 1400 m/s while the tube wave velocity in 205 and 209 is 1380 m/s There is a 10 m thick permeable layer 207 near the bottom 211. 213 and 215 shows pressure simulations at the top, middle and bottom of the borehole. Compared FIG. 5b to FIG. 2, the amplitude decay is more rapid and the wave shape exhibits some distortions.

We here apply the generalized R/T coefficients method to study dispersion relations of tube waves, or normal modes, in fluid-filled boreholes shown in FIG. 4a. The radial layers can be any combination of liquid, non-permeable solid, and permeable porous media. Solving of the dispersion relation will give the velocity and attenuation for a normal mode of interest.

Three types of media, fluid, non-permeable solid, and permeable porous solid, are involved in this problem. Therefore, we need to deal with liquid-solid, liquid-porous, solid-solid, solid-porous, solid-liquid, porous-liquid, porous-porous and porous-solid boundary conditions. Let $u^{(j)}$ be the displacement-stress vector for the $j^{th}$ layer in radial direction, which is represented by $$u^{(j)} = E_-^{(j)} c_-^{(j)} + E_+^{(j)} c_+^{(j)}, \quad (7)$$

where $E_\pm^{(j)}$ are the general solutions of wave equations and $c_\pm^{(j)}$ are unknown coefficients to be determined by the generalized R/T coefficients method for given boundary conditions. '+' and '−' signs refer to outgoing and incoming waves, respectively. The length of u is 2 for liquid, 4 for non-permeable solid, 6 for permeable porous solid. The reflection and transmission coefficients at boundary $r=r^{(j)}$ can be expressed as $$\begin{bmatrix} R_{+-}^{(j)} & T_{-}^{(j)} \\ T_{+}^{(j)} & R_{-+}^{(j)} \end{bmatrix} = [E_-^{(j)} \ -E_+^{(j+1)}]^{-1}[-E_+^{(j)} \ E_-^{(j+1)}]. \quad (8)$$

Generalized reflection and transmission coefficients, $\hat{R}_\pm^{(j)}$ and $\hat{T}_+^{(j)}$, are defined through $$c_-^{(j)} = \hat{R}_\pm^{(j)} c_+^{(j)} \text{ and } c_\pm^{(j+1)} = \hat{T}_+^{(j)} c_+^{(j)}, \quad (9)$$

and can be obtained from iteration relations $$\begin{cases} \hat{T}_+^{(j)} = [I - R_{-+}^{(j)} \hat{R}_{+-}^{(j+1)}]^{-1} T_+^{(j)} \\ \hat{R}_{+-}^{(j)} = R_{+-}^{(j)} + T_-^{(j)} \hat{R}_{+-}^{(j+1)} \hat{T}_+^{(j)} \end{cases} \quad (10)$$

with initial condition $$\hat{R}_\pm^{(N+1)} = 0. \quad (11)$$

Equation (11) means that there only exist outward-going waves in the outer-most layer N+1.

The normal modes are the non-trivial solutions of the source-free wave equation under given boundary conditions. The requirement of a non-trivial solution leads to the dispersion relation $$1 - \hat{R}_\pm^{(1)}(\omega, k, m) = 0. \quad (12)$$

The first layer is fluid and only P-wave exists. Therefore, the generalized reflection coefficient $\hat{R}_\pm^{(1)}$ in this layer is reduced to a scalar. $\hat{R}_\pm^{(1)}$ is a function of angular frequency $\omega$, wave-number k, and borehole model parameter vector m. We solve eqn (12) numerically. For a given real $\omega$ we search for the complex wave-number k that is the root of eqn (12). The real part of k gives phase velocity $c = \omega/k_r$ and the imaginary part gives Q-value $Q = 0.5\, k_r/k_i$. The complex wave-number k is substituted into eqns (5) and (6), or used in the propagator matrix method for calculation of reflection and transmission coefficients in the wave hammer wave simulation.

Figure 6B:
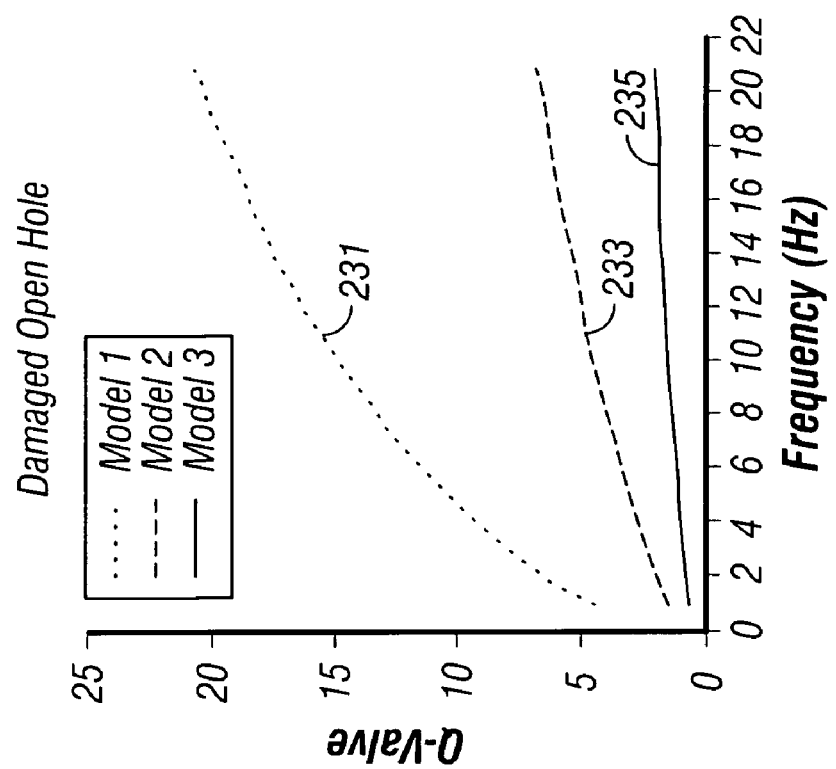
FIGS. 6a and 6b shows dispersion curves and Q of boreholes with multi-layered porous media.
Figure 6A:
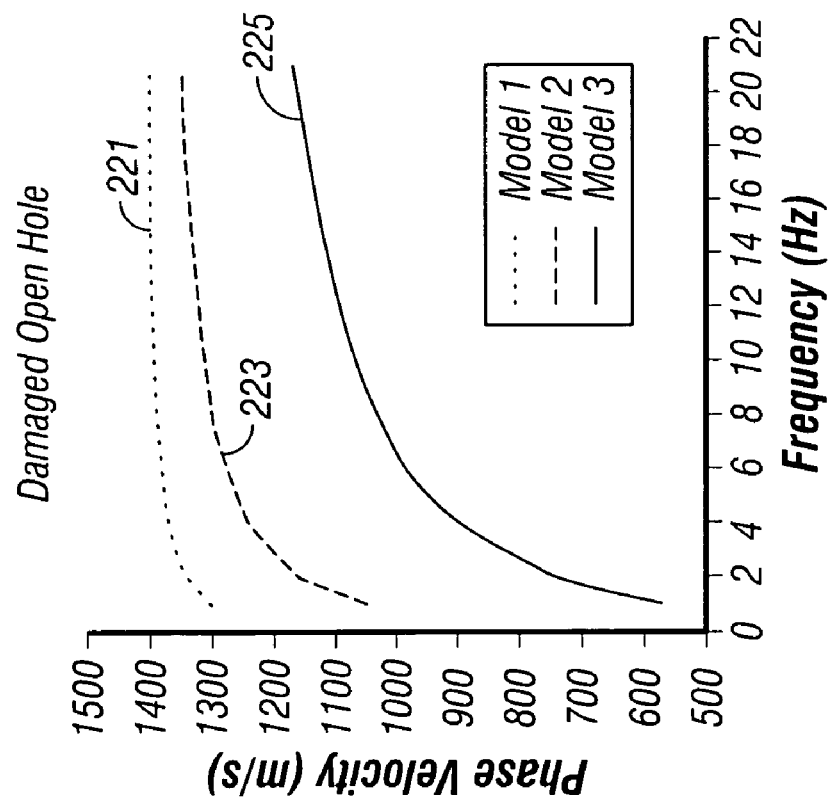

FIGS. 6a and 6b shows the dispersion curves for three porous models. The curves 221, 223 and 225 in FIG. 6a are the phase velocities for models 1, 2 and 3 respectively while curves 231, 233 and 235 are the quality factors Q for the three models. The model parameters are given in Table 1. It can be seen from FIG. 6a that the dispersion curve is very sensitive to the permeability in the low frequency range that the water hammer waves hold. We may expect that water hammer is useful for well testing, especially the estimation of permeability and porosity. Specifically, the geometry of the vertical layering is usually known, as are the compressional and shear velocities. A variety of synthetic outputs may be generated for a range of porosities and a table look-up performed to estimate the permeability.

Figure 7A:
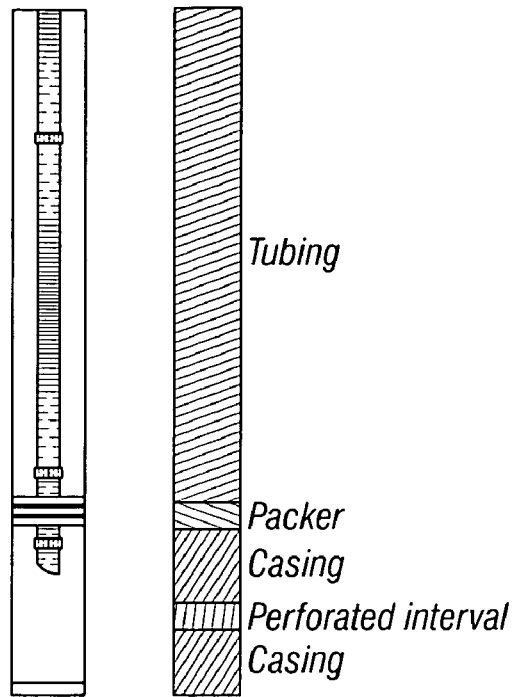
FIG. 7a shows a schematic vertical diagram of a well including tubing, packer, casing and a perforated interval.
Figure 7B:
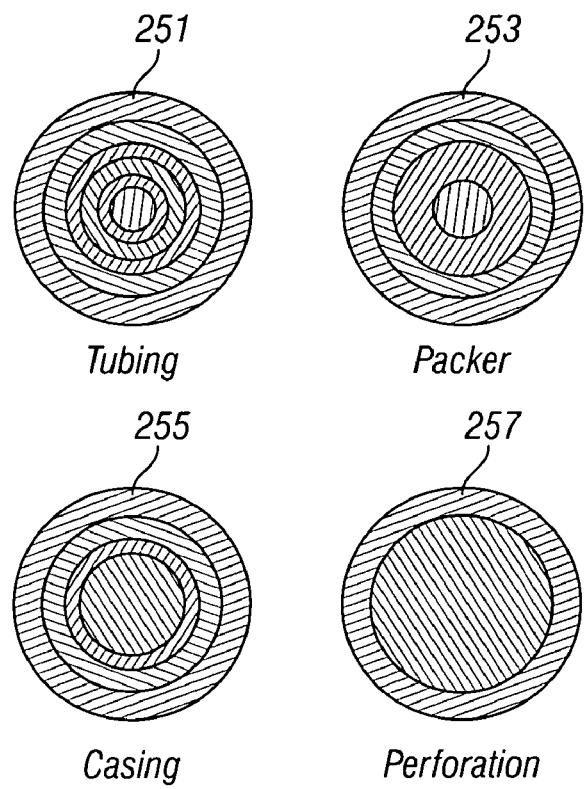
FIG. 7b shows a horizontal section of the well of FIG. 7a at different depths.

We next examine a completed well containing tubing accessing a single perforated interval in the earth. FIG. 7a is a schematic vertical section of the arrangement showing tubing, packer and a casing including a perforated interval. Horizontal cross sections corresponding to the different intervals are shown in FIG. 7b. The perforated interval is depicted by 257. The interval having tubing is depicted by 251 the interval having the packer is denoted by 253 while the cased interval is denoted by 255. The water hammer is simulated by defining a model that has a plurality of horizontal layers wherein one or more of the horizontal layers may also have radial layering. It should be noted that, following common practice in the industry, the terms "horizontal" and "vertical" may be relative to the borehole itself.

The particular examples shown in this document were modeled with the borehole being perpendicular to the horizontal layers. This is not to be construed as a limitation to the invention and the method may be used with some modification when the borehole is not perpendicular to the layers. Such a situation of inclined bedding can be simulated by adding azimuthal terms in the modeling.

Figure 7C:
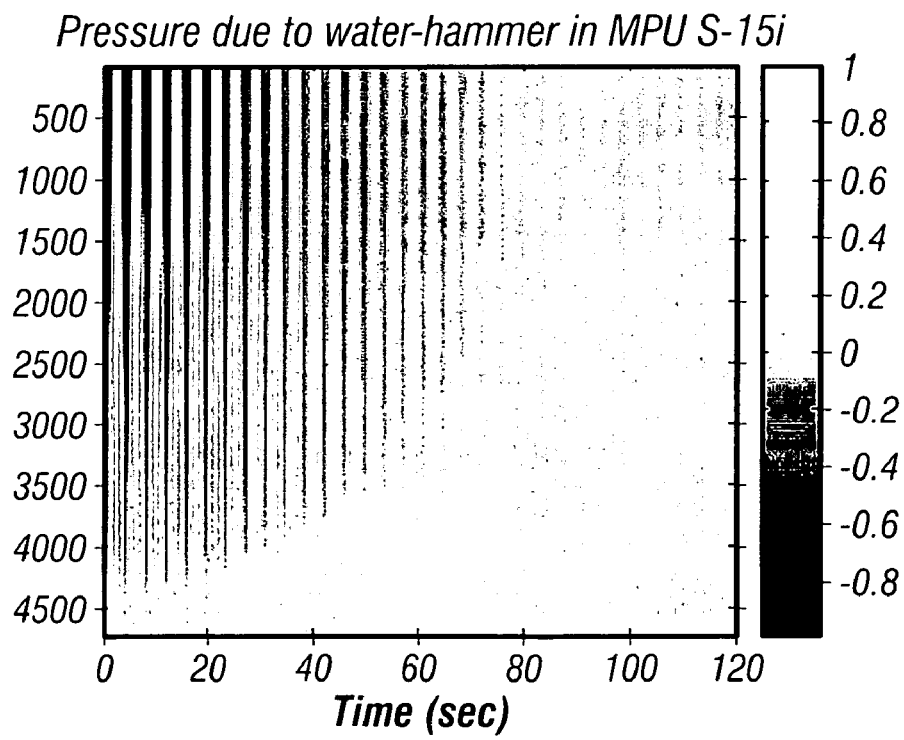
FIG. 7c shows the pressure field of the well of FIG. 7a to a water hammer.
Figure 8A:
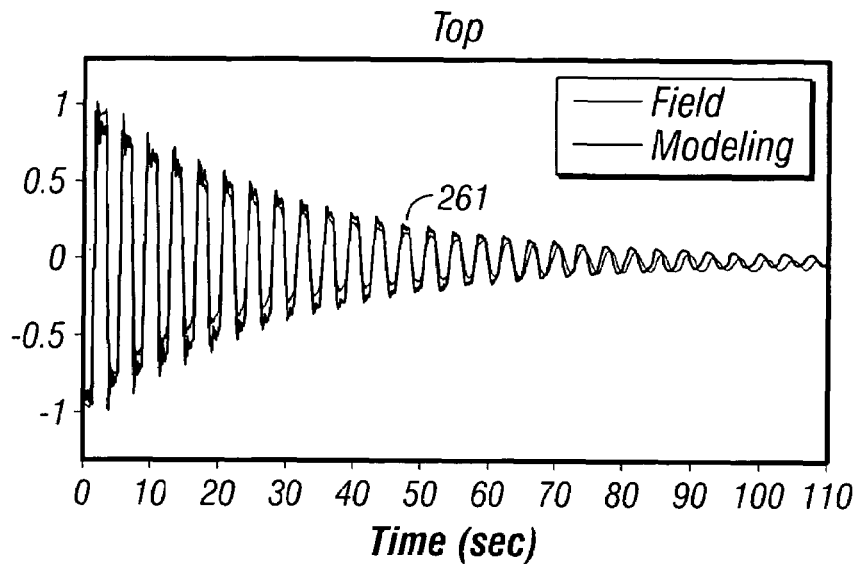
FIGS. 8a-8c show comparisons of a simulated pressure data with measured field data at the top, middle and bottom of a well.
Figure 8B:
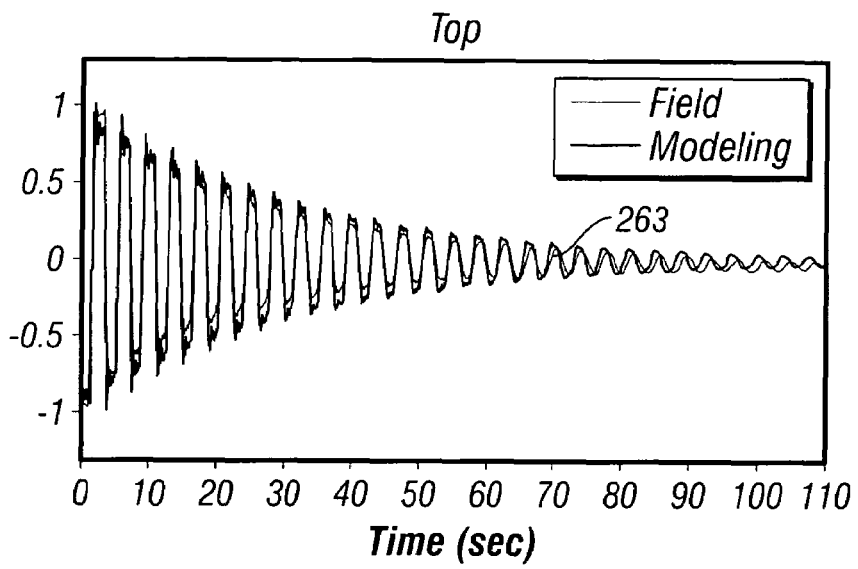
Figure 8C:
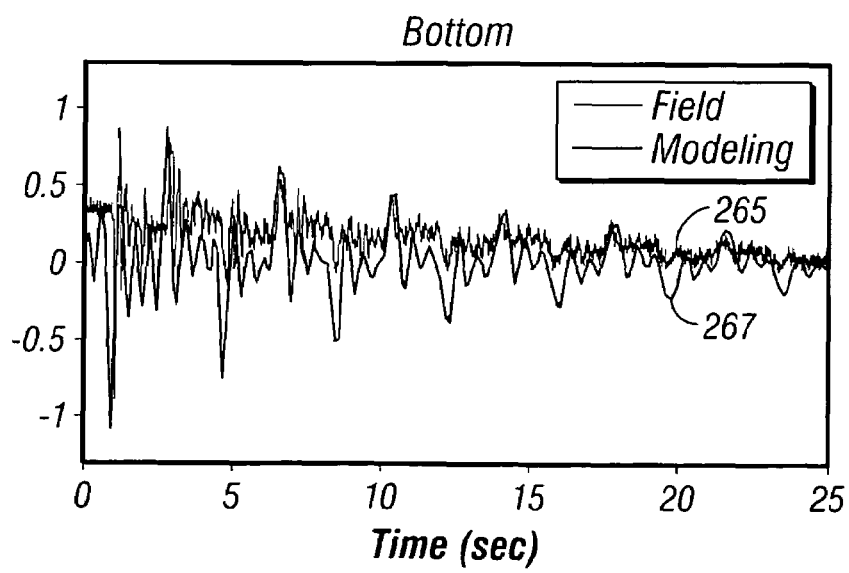

FIG. 7c shows the decay of a water hammer. The abscissa is time while the ordinate is depth. 261 in FIG. 8a is a time domain representation of the simulated water hammer signal and actual field measurements made in a well for which the model is shown in FIG. 7a-7b. Due to the excellent agreement between the simulated and the measured signals, a single curve suffices. The same is true of FIG. 8b which shows simulated and actual measurements 263 made in the same borehole at the middle of the interval. The difference between the simulated 267 and measured pressure 265 is noticeable near the bottom of the interval in FIG. 8c. It should be noted that for the example shown, the water hammer near the bottom is an order of magnitude smaller than at the top of the well. The difference arises mainly due to a mismatch at the very low frequencies. In an alternate embodiment of the invention, the low frequency mismatch may be corrected. Referring now to FIGS. 9-14, there are shown illustrative applications of the method described above.

Figure 9A:
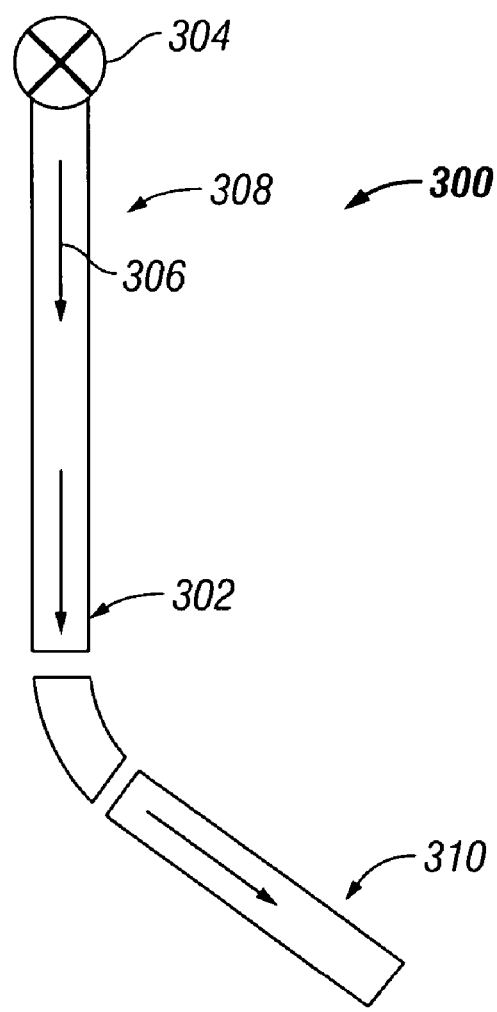
FIG. 9a schematically illustrates an exemplary completion system wherein water-hammer propagate with limited energy loss and wave dispersion.

FIG. 9a schematically illustrates the effect of transmission of a water-hammer along a monobore well 300 wherein a steel casing 302 of a substantially constant diameter has been installed and is cemented throughout. A valve or other flow restrictor 304, when actuated, generates a wave 306 that propagates from a first location 308 to a second location 310 lower in the well 300. The wave propagation characteristics are a function of various parameters including borehole dimensions (e.g., hole size), shape and material make-up of borehole tubing, cement properties, fluid prop-

TABLE 1

Model parameters of boreholes in multi-layering porous media

Figure 9B:
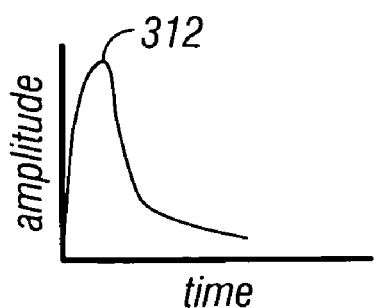
Figure 9C:
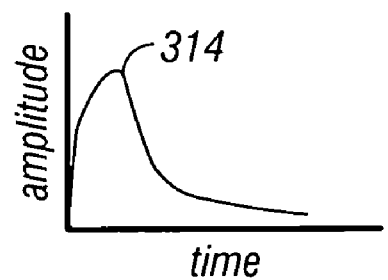

| | r (cm) | $V_p$ (m/s) | $V_s$ (m/s) | $\phi$ (%) | $\kappa$ (mD) | $\eta$ (poise) | $\rho_s$ (g/cm$^3$) | $\rho_f$ (g/cm$^3$) |
|---|---|---|---|---|---|---|---|---|
| Layer 1 | 7.62 | 1500 | — | — | — | — | — | 1.0 |
| Layer 2 | 61 | 4700 | 3000 | 20 | | $10^{-3}$ | 2.65 | 1.0 |
| Model 1 | | | | | 2 | | | |
| Model 2 | | | | | 20 | | | |
| Model 3 | | | | | 200 | | | |
| Layer 3 | — | 3970 | 2460 | 20 | | 1 | 2.65 | 1.0 |
| Model 1 | | | | | 20 | | | |
| Model 2 | | | | | 200 | | | |
| Model 3 | | | | | 2000 | | | | erties, and coupling properties. FIGS. 9b and 9c illustrate exemplary waveforms or shapes 312 and 314 at the first location 308 and 310, respectively. As can be seen, there is relatively small change in wave amplitude for wave shapes 312 and 314, which indicates that energy transmitted by the waves encountered relatively little propagation loss. Thus, in this completion arrangement, the casing 302, being free of sections or features that attenuate, reflect or absorb energy, allows transmission of waves with low attenuation and low dispersion. Thus, these waves 306 have relatively high energy and impulsive arrival at the second location 310.

A common reason why a valve at the surface may be suddenly closed is if there is an indication of a sudden pressure change in the borehole, This may be caused, for example, by a sudden influx of gas. The valve may be part of a blowout preventer (BOP) which is closed rapidly to avoid a catastrophic blowout of the well. The conventional wisdom has been that the BOP should be operated as quickly as possible. The present invention makes it possible to analyze the effect of such a sudden operation of the BOP in terms of pressure waves within the borehole. In some instances, the pressure due to the water hammer may exceed the borehole strength in some intervals. With the present invention, it is possible to simulate a not-so-rapid closing of the BOP: instead of a step function, a ramp function may be used and BOP operation may then be done with the formation strength taken into consideration. The same applies to opening of a flow control device, which can have the same change in kinetic energy as is involved in closing a flow control device. It should be noted that downhole electronics, electrical equipment and electromechanical equipment may likewise by susceptible to damage from excessive pressure and the present invention makes it possible to provide a measure of protection.

Figure 10A:
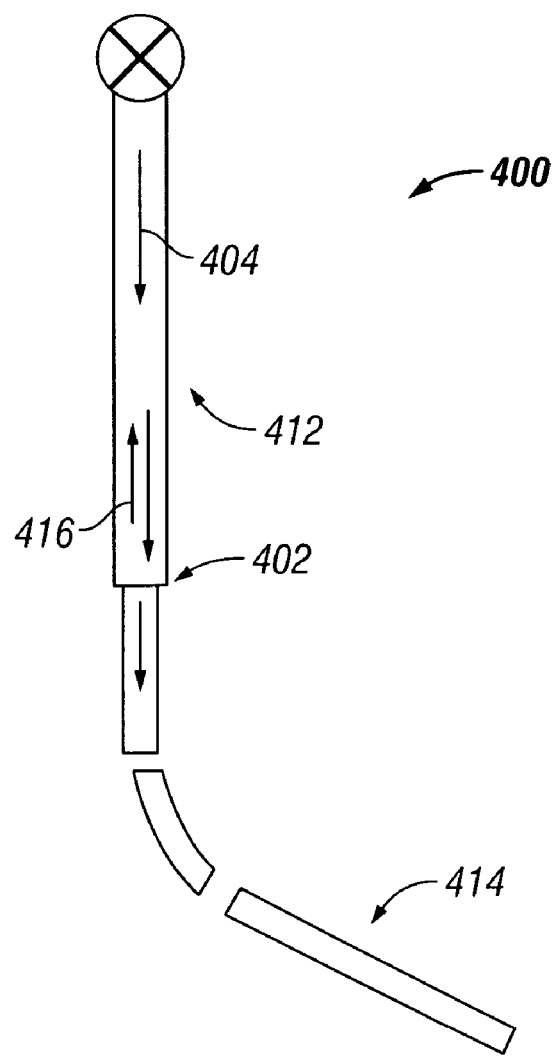
FIG. 10a schematically illustrates an exemplary completion system utilizing a wave reflector in accordance with one embodiment of the present invention that reduces the energy in waves propagating along the completion system.
Figure 10B:
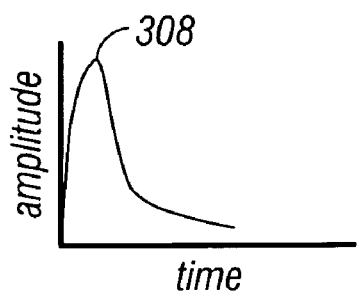
Figure 10C:
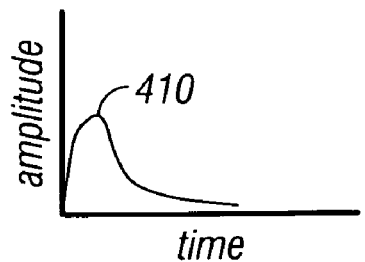

FIG. 10a schematically illustrates a completion arrangement wherein a tubular string 400 includes a wave reflector section 402 adapted to reflect waves traveling through the string 400. To control waves 404 propagating through the string 400, the wave reflector section 402 has a reduced diameter that generates a wave reflection 416, which thereby reduces the energy transmitted into the borehole below the wave reflector section 402. It should be appreciated that the configuration of the wave reflector section 402, such as shape (e.g., stepped reduction, graduated reduction, etc.), dimension, material make-up, can be selected to control the characteristics of the reflected wave 416. FIGS. 10b and 10c illustrate exemplary wave shapes 408 and 410 at a first location 412 uphole of the wave reflector section 402 and a second location 414 downhole of the wave reflector section 402, respectively. As can be seen, energy reflected by the section 402 reduces the amplitude of the waves 404 traveling past the section 402.

Figure 11A:
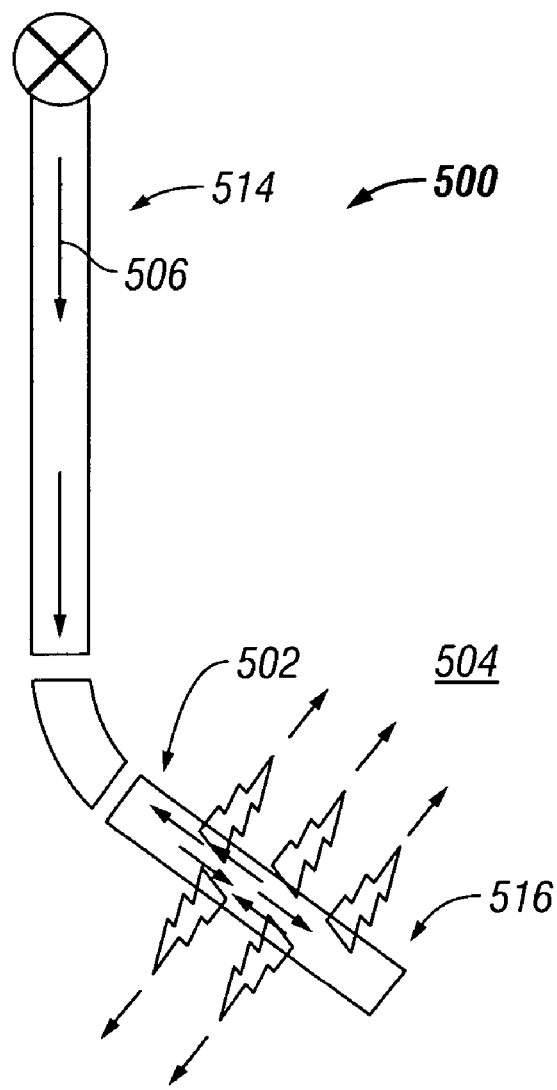
FIG. 11a schematically illustrates an exemplary completion system utilizing a wave attenuator in accordance one embodiment of the present invention that reduces the energy in waves propagating along the completion system.
Figure 11B:
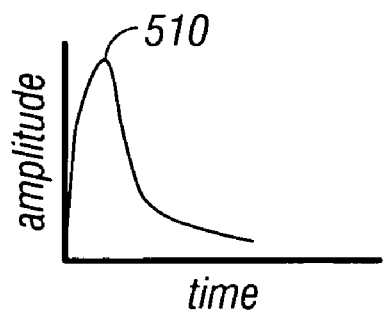
Figure 11C:
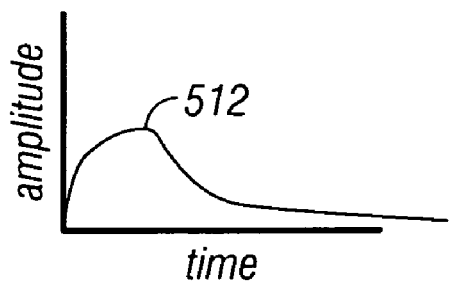

FIG. 11a illustrates completion arrangement wherein a tubular string 500 has been provided with a wave attenuator section 502, which has a plurality of perforations 503. The characteristics of the attenuator section 502 are selected to transmit wave energy into the adjacent formation 504. For example, the size, shape, dispersion and other aspects of the perforations 503 can be selected to optimize wave attenuation. Thus, as waves 506 propagate along the string 500, the waves 506 interact with the wave attenuator section 502, which then transmits some wave energy from the tubular string 500 into the formation 504. Thus, the attenuator section 502 causes an increase in attenuation as the wave 506 passes each perforation 503. FIGS. 11b and 11c illustrate an exemplary wave shapes 510 and 512 at a first location 514 uphole of the wave attenuator section 502 and a second location 516 downhole of the wave attenuator section 502, respectively. As can be seen, energy attenuated by the section 502 reduces the amplitude of the waves traveling past the section 502 as well as increases the dispersion of the waves.

Figure 12A:
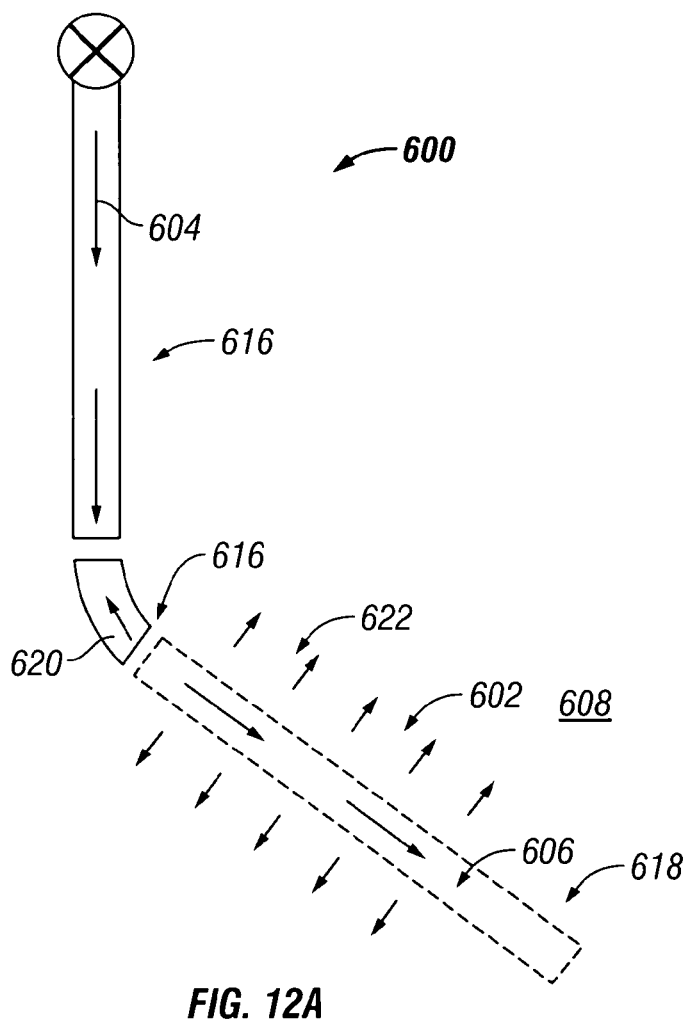
FIG. 12a schematically illustrates an exemplary completion system utilizing a wave absorber in accordance one embodiment of the present invention that reduces the energy in waves propagating along the completion system
Figure 12B:
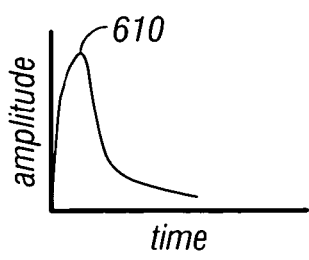
Figure 12C:
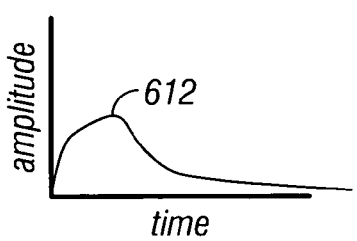
Figure 12D:
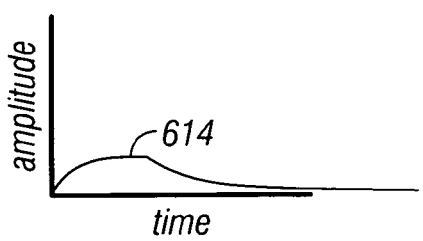

FIG. 12a illustrates completion arrangement wherein a tubular string 600 has been provided with a wave absorption section 602 that exposes the borehole 606 to an adjacent permeable formation 608. The section 602 can include a screen, a gravel-pack, or other device or can an open-hole completion. The section 604 is configured to couple the fluid in the borehole 606 to the formation and thereby allow wave energy to be absorbed by the adjacent formation 608. FIGS. 11b, 11c, and 11d respectively illustrate an exemplary wave shape 610 at a first location 616 uphole of the wave attenuator section 602, an exemplary wave shape 612 at a second location 618 approximately at an uphole end of the absorption section 602, and an exemplary wave shape 614 at a third location 620 downhole of the absorption section 602. At the second location 616, a transition between the casing and the absorption section 602 generates reflected waves 620 that reduce wave energy and increases wave dispersion, which is shown in the reduced amplitude of wave shape 612 as compared to wave shape 610. Thereafter, energy attenuated by the section 602 reduces the amplitude of the waves traveling past the section 602 as well as disperses these waves, the dispersion being shown with numeral 622, which is shown in the reduced amplitude of wave shape 612 as compared to wave shape 614.

Figure 13A:
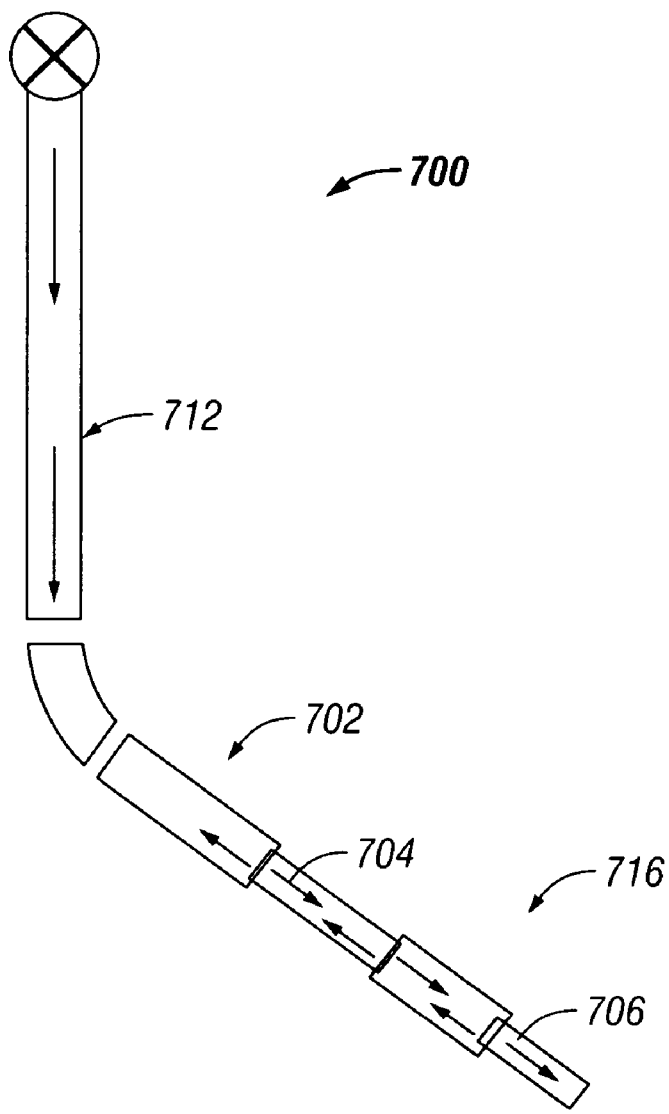
FIG. 13a schematically illustrates an exemplary completion system utilizing an attenuator in accordance one embodiment of the present invention that reduces the energy in waves propagating along the completion system.
Figure 13B:
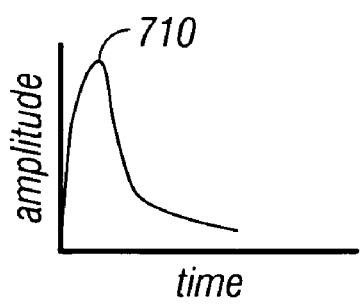
Figure 13C:
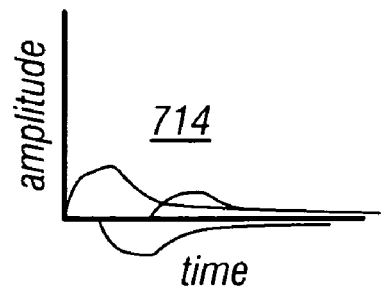

Referring now to FIG. 13, there is schematically illustrated an exemplary attenuator 700 constructed according to embodiments of the present invention for use in a completion system 702. The attenuator 700 can be a tubular member that includes a plurality of reduced diameter sections 704 and 706 that are juxtaposed along a length of a borehole. For example, the attenuator 700 can include a section of expandable liner or casing. Selected sections of the liner or can be expanded at discrete intervals. The interval lengths are selected based on optimizing destructive interference of the transmitted wave. The wave modeling methods discussed above can be utilized to select factors such as the dimensions of the diameter reductions, the interval distances and number of diameter reductions. FIGS. 13b and 13c respectively illustrate an exemplary wave shape 710 at a first location 712 uphole of the wave attenuator 700 and an exemplary wave shape 712 at a second location 714 generally along the wave attenuator 700. As can be seen, waves 720 traveling along the completion system 702 are subjected to multiple, destructively interfering reflections along the attenuator 700, which reduces the energy level of the waves traveling downhole past the attenuator 700. Other attenuators could be created by exposing sections of formation across screens, by selectively perforating sections of tubing, and by other methods and devices.

Figure 14:
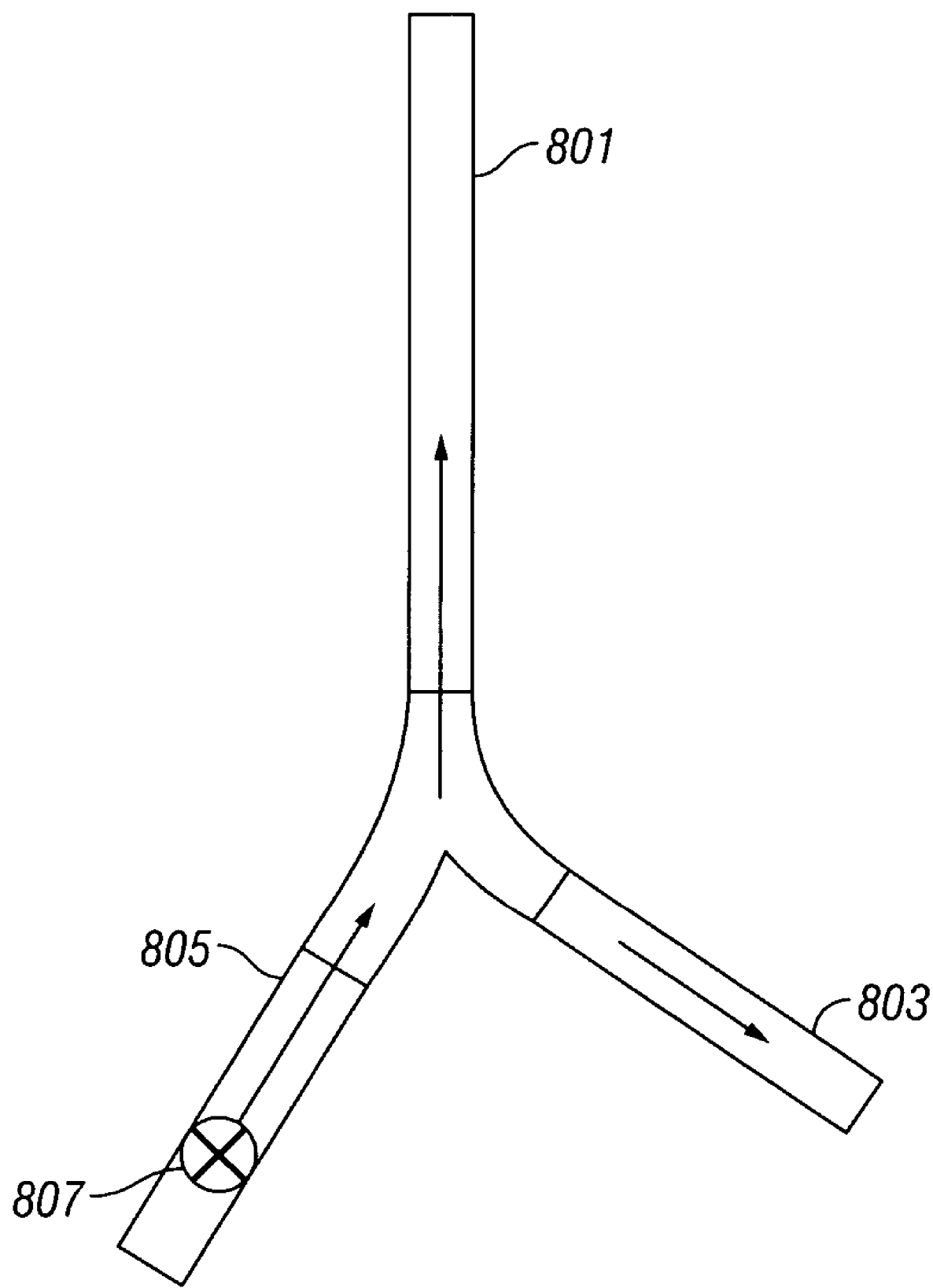
FIG. 14 shows a flow control device in a side borehole.

FIG. 14 shows an arrangement in which there are two sidebores 803, 805 that branch out from a main borehole 801. As an example, a flow control device 807 is depicted in the sidebore 805. The operation of a flow control device can generate a water hammer just as the operation of the flow control device 304 shown in FIG. 9a at the surface. This water hammer can propagate up the main borehole as well as into the sidebore 803. Accordingly, the same devices discussed above with reference to FIGS. 9-13 may also be used, and design of the completion string would be governed by the same principles discussed above.

With the method of the present invention, it is possible to simulate the effects of the length of perforation tunnels; width and hydraulic properties of a fracture and shut-in procedures (methods to shut in w/o excessive risk to completion and formation).

The principles discussed above for simulation of the water hammer may also be used for determination of formation properties. This is illustrated with reference to FIGS. 15a-15f. Shown in FIG. 15a are simulated responses to a water hammer in a cased home with 200 m of smaller casing below the casing. The simulated pressure signal is shown at the top, middle and bottom of the hole. By way of comparison, FIG. 15b shows corresponding waveforms when there is 200 m of open hole in a formation of permeability 0.5 mD below the cased hole. Some decrease in amplitude of the signals is noted at the deepest level between the hole with smaller casing (FIG. 15a) and the open hole (FIG. 15b).

FIG. 15c shows corresponding signals when the open hole section has a permeability of 5 mD. The decrease in signal amplitude compared to FIG. 15b is significant. The decrease is even more dramatic in FIG. 15d wherein the open-hole section has a permeability of 500 mD. The frequency content and the amplitude of the water hammer signal is thus indicative of formation permeability and porosity.

FIG. 15e shows the water hammer when there is 200 m of open hole (permeability of 30 D) that includes a 10 cm damaged zone with permeability of 20 mD. The water hammer signal is significant, showing that it is indicative of possible formation damage. Finally, FIG. 15f shows the water hammer for 200 m of open hole (300 mD) with 1 cm of a damaged zone with permeability 20 mD. Thus, formation damage has an effect on the water hammer just as formation porosity and formation permeability do.

In another embodiment of the invention, the borehole system may be monitored over a period of time. Due to production from one or more layers as a function of time, some of the formation properties may change. When sand control devices are used, their effectiveness may deteriorate with time. Monitoring the wellbore system by making measurements of a water hammer over an extended period of time may identify such formation and or completion-device changes, and suitable remedial action may be taken. Thus, the method of the present invention is useful not only for the initial design of well-completion systems, but also for continued development of the reservoir.

To summarize, the present invention teaches methods and devices that utilize analytical techniques for characterizing water-hammer to configure borehole completion equipment that mitigate the harmful effects of water-hammer. In exemplary application, known factors and properties such as formation parameters, fluid parameters, tubular dimensions, and completion properties are utilized to characterize wave propagation. Such modeling can be used both to calculate the effects of a known amplitude water hammer as a function of distance from its source, and to develop methods to reduce the amplitude of the wave at a completion, thereby reducing the likelihood of formation damage (liquifaction, for example) due to a pressure pulse. Examples of the types of completion that can be analyzed in via modeling include perforations, characteristics of borehole tubulars (e.g., changes in size, shape, number, cementation, etc.), objects inserted into the well at critical locations either concentrically or eccentrically in the well, the effects of compliant and noncompliant screens and of gravel-pack and open-hole completions, frac-packs and fracture stimulations in formations with various properties (porosities, permeabilities, and frame elastic/viscoelastic properties and strength).

The characteristics of a water hammer at the point where it is generated are either calculated using established methods, or can be assumed for purposes of evaluating only the propagation characteristics of the well bore. The reflectivity and specific attenuation as a function of frequency and of completion/formation/borehole properties can be determined using theories for the propagation of Stoneley waves.

The effects of a variety of parameters of which a subset are listed below are modeled by computing the complex, frequency-dependent velocity, from which specific attenuation (e.g., in dB/meter) is derived as a function of frequency. Transformation from the frequency-wave number domain to the time-distance domain makes it possible to plot the amplitude and shape of the water-hammer pulse as a function of distance traveled along the well.

Frequency-dependent reflectivity from reflectivity contrasts is computed by determining the impedance of adjacent configurations, and computing the complex reflection and transmission coefficients as a function of frequency that result from their juxtaposition. By making measurements of the pressure signal at different depths along a borehole, it is possible to estimate formation properties such as permeability, and to identify possible formation damage. Analysis of fractures and perforations may be carried out using analysis of the water hammer. While the invention has been described above in the context of sudden changes in pressure by operation of a flow control device, it should be noted that a water hammer may also be produced as a result of pressure drawdown and pressure buildup tests as the terms are understood by those versed in the art.

Those versed in the art would recognize that measurements of fluid flow in the borehole are indicative of and track the fluid pressure. This is particularly true if a flow measurement system is that does not have a significant effect on the propagation of the water hammer. Such a flow measurement system could include mechanical, electrogalvanic, heat pulse and/or radioactive tracer type meters.

The processing of the data may be accomplished by a downhole processor. Implicit in the control and processing of the data is the use of a computer program implemented on a suitable machine-readable medium that enables the processor to perform the control and processing. The machine-readable medium may include ROMs, EPROMs, EAROMs, flash memories and/or optical disks. These are all media that can store large amounts of data and/or instructions, are suitable for use at surface locations and with some exception, suitable for use downhole.

What is claimed is:

1. A method of determining a property of an earth formation, the method comprising:
   (a) generating a fluid hammer in a borehole in the earth formation, the fluid hammer producing a pressure pulse in the fluid, the pressure pulse propagating in the borehole at velocity determined at least in part by a shear velocity of the formation;
   (b) making a measurement indicative of a pressure of the fluid at at least one location in the borehole;
   (c) estimating a value of the property of the formation using the measured fluid pressure and a model of the borehole and the earth formation, the model including a plurality of layers, at least one of the plurality of layers including concentric radial layering; and
   (d) using the estimated value of the property in development of the borehole.

2. The method of claim 1 wherein generating the fluid hammer further comprises at least one of (i) opening a flow control device and (ii) closing a flow control device.

3. The method of claim 1 wherein estimating the property of the formation further comprises simulating an output of the model and comparing the simulated output with the measurement.

4. The method of claim 3 wherein simulating the output of the model further comprises using reflection and transmission coefficients.

5. The method of claim 1 wherein the property further comprises at least one of (i) a formation permeability, (ii) a formation porosity, and (iii) a damage to the formation.

6. The method of claim 1 further comprising:
   (i) repeating steps (a) and (b) at a later time; and
   (ii) determining a change in the value of the property.

7. The method of claim 1 wherein making the measurement comprises at least one of (i) measuring a pressure of the fluid, and (ii) measuring a rate of flow of the fluid.

8. A method of developing a reservoir in an earth formation, the method comprising:
   (a) defining a model of the earth formation and a borehole therein, the model including a plurality of layers, at least one of the plurality of layers including concentric radial layering;
   (b) simulating an output of the model to a fluid hammer in the borehole, the fluid hammer comprising a pressure pulse propagating in the borehole at a velocity determined at least in part by a shear velocity of the formation; and
   (c) using the output to perform a completion operation in the borehole.

9. The method of claim 8 further comprising operating a flow control device at at least one of (i) a surface location, (ii) a downhole location, and (iii) a downhole location in a side borehole.

10. The method of claim 8 wherein performing the completion operation further comprises determining a parameter of a completion string selected from (i) borehole diameter, (ii) borehole shape, (iii) material of a casing, (iv) material of a tubing, (v) a property of a cement, (vi) a property of a fluid in the borehole, and (vii) a property of a coupling between two sections of casing.

11. The method of claim 8 wherein performing the completion operation further comprises determining a parameter of a completion string selected from (i) a wave reflector section, and (ii) a wave attenuator section.

12. The method of claim 8 wherein performing the completion operation further comprises determining a parameter of a completion string selected from (i) a screen, and (ii) a gravel-pack.

13. The method of claim 8 wherein performing the completion operation further comprises determining a parameter of a completion string selected from (i) a dimension of a diameter change, (ii) an interval distance between diameter changes, and (iii) a number of diameter changes.

14. A computer readable medium for use with a method of determining a property of the earth formation, the method comprising:
   (a) generating a fluid hammer in a borehole in the earth formation, the fluid hammer producing a pressure pulse in the fluid, the pressure pulse propagating in the borehole at velocity determined at least in part by a shear velocity of the formation; and
   (b) making a measurement indicative of pressure of the fluid at at least one location in the borehole,
   the medium comprising instructions that enable a processor to:
   (c) estimate a value of the property of the formation using the measurement and a model of the borehole and the earth formation, the model including a plurality of layers, at least one of the plurality of layers including concentric radial layering; and
   (d) use the estimated value of the property in development of the borehole.

15. The medium of claim 14 further comprising at least one of (i) a ROM, (ii) an EPROM, (iii) an EAROM, (iv) a flash memory, and (v) an optical disk.

16. The medium of claim 14 wherein the instructions further enable the processor to determine a property that is at least one of (i) a permeability, (ii) a porosity, and (iii) a damage to a formation.

* * * * *